(12) United States Patent
Khetani et al.

(10) Patent No.: US 12,180,507 B2
(45) Date of Patent: Dec. 31, 2024

(54) ENGINEERED PLATFORMS TO STABILIZE BOTH HEPATOCYTES AND ENDOTHELIAL CELLS IN VITRO

(71) Applicant: Colorado State University Research Foundation, Fort Collins, CO (US)

(72) Inventors: Salman R. Khetani, Chicago, IL (US); Mitchell J. Durham, Fort Collins, CO (US); Brenton R. Ware, Chicago, IL (US)

(73) Assignee: Colorado State University Research Foundation

( * ) Notice: Subject to any disclaimer, the term of this patent is extended or adjusted under 35 U.S.C. 154(b) by 390 days.

(21) Appl. No.: 15/749,733

(22) PCT Filed: Aug. 5, 2016

(86) PCT No.: PCT/US2016/045719
§ 371 (c)(1),
(2) Date: Feb. 1, 2018

(87) PCT Pub. No.: WO2017/024206
PCT Pub. Date: Feb. 9, 2017

(65) Prior Publication Data
US 2018/0223253 A1 Aug. 9, 2018

Related U.S. Application Data

(60) Provisional application No. 62/201,166, filed on Aug. 5, 2015.

(51) Int. Cl.
| | |
|---|---|
| *C12N 5/00* | (2006.01) |
| *A61K 35/407* | (2015.01) |
| *A61K 35/44* | (2015.01) |
| *C12N 5/071* | (2010.01) |
| *G01N 33/50* | (2006.01) |

(52) U.S. Cl.
CPC ............ *C12N 5/067* (2013.01); *A61K 35/407* (2013.01); *A61K 35/44* (2013.01); *G01N 33/5014* (2013.01); *C12N 2502/1323* (2013.01); *C12N 2502/28* (2013.01); *C12N 2503/02* (2013.01); *C12N 2533/52* (2013.01); *C12N 2533/54* (2013.01); *C12N 2533/90* (2013.01); *C12N 2535/10* (2013.01)

(58) Field of Classification Search
CPC .............................. C12N 5/067; C12N 2502/14
See application file for complete search history.

(56) References Cited

U.S. PATENT DOCUMENTS

| | | | |
|---|---|---|---|
| 6,133,030 A | 10/2000 | Bhatia et al. | |
| 8,580,248 B2 | 11/2013 | Elliott et al. | |
| 8,617,815 B2 | 12/2013 | Khetani et al. | |
| 8,778,607 B2 | 7/2014 | Sokal et al. | |
| 10,266,806 B2 * | 4/2019 | Khetani et al. | ........ C12N 5/067 |
| 10,717,966 B2 | 7/2020 | Khetani et al. | |
| 2001/0023073 A1 | 9/2001 | Bhatia et al. | |
| 2003/0003573 A1 | 1/2003 | Rambhatle et al. | |
| 2006/0199172 A1 | 9/2006 | Aikawa et al. | |
| 2006/0270032 A1 | 11/2006 | Bhatia et al. | |
| 2008/0233607 A1 | 9/2008 | Yu | |
| 2011/0262956 A1 | 10/2011 | Elias et al. | |
| 2011/0318730 A1 | 12/2011 | Rice, III et al. | |
| 2012/0111795 A1 | 5/2012 | Chamuleau et al. | |
| 2013/0164266 A1 | 6/2013 | Jensen | |
| 2013/0266939 A1 * | 10/2013 | McVay et al. | ..... G01N 33/5088 435/6.11 |
| 2013/0309677 A1 | 11/2013 | Blackman et al. | |
| 2014/0212918 A1 | 7/2014 | Yarmush | |
| 2015/0079673 A1 | 3/2015 | Khetani et al. | |
| 2015/0240203 A1 * | 8/2015 | Khetani et al. | ........ C12N 5/067 |
| 2016/0252494 A1 | 9/2016 | Bhatia et al. | |

FOREIGN PATENT DOCUMENTS

| | | |
|---|---|---|
| WO | 98/51785 A1 | 11/1998 |
| WO | 2012/119012 A1 | 9/2012 |

OTHER PUBLICATIONS

Liu et al. "Hepatocyte Cocultures with Endothelial Cells and Fibroblasts on Micropatterned Fibrous Mats to Promote Liver-Specific Functions and Capillary Formation Capabilities", Biomacromolecules 2014, 15, 1044-1054. (Year: 2014).*
Nahmias et al. "Endothelium-Mediated Hepatocyte Recruitment in the Establishment of Liver-like Tissue In Vitro", Tissue Engineering, vol. 12, No. 6, 2006, pp. 1627-1638. (Year: 2006).*
Hughes et al. "Matrigel: A complex protein mixture required for optimal growth of cell culture", Proteomics 2010, 10, 1886-1890. (Year: 2010).*
March et al. "Microenvironmental Regulation of the Sinusoidal Endothelial Cell Phenotype In Vitro", Hepatology, vol. 50, No. 3, 2009, pp. 920-928. (Year: 2009).*
Supplemental Material of March et al. "Microenvironmental Regulation of the Sinusoidal Endothelial Cell Phenotype In Vitro", Hepatology, vol. 50, No. 3, 2009, pp. 920-928. (Year: 2009).*
Khetani et al. "Microscale culture of human liver cells for drug development", Nature Biotechnology, vol. 26, No. 1, 2008, pp. 120-126. (Year: 2008).*
Liu et al. "Hepatocyte Cocultures with Endothelial Cells and Fibroblasts on Micropatterned Fibrous Mats to Promote Liver-Specific Functions and Capillary Formation Capabilities", Biomacromolecules 2014, 15, 1044-1054 (published Feb. 2014). (Year: 2014).*
Salerno et al. "Human hepatocytes and endothelial cells in organotypic membrane systems" Biomaterials 32 (2011) 8848-8859. (Year: 2011).*
Jindal et al. (2009) "Amino acid-mediated heterotypic interaction governs performance of a hepatic tissue model" The FASEB journal, 23(7), 2288-2298. (Year: 2009).*

(Continued)

*Primary Examiner* — Teresa E Knight
*Assistant Examiner* — James Joseph Graber
(74) *Attorney, Agent, or Firm* — The Belles Group, P.C.

(57) ABSTRACT

The disclosure relates to in vitro cultures of human hepatocytes, and in particular co-cultures systems including human hepatocytes, non-parenchymal cells, and human endothelial cells, and the use of the co-cultures in developing and screening drugs.

13 Claims, 11 Drawing Sheets
(5 of 11 Drawing Sheet(s) Filed in Color)
Specification includes a Sequence Listing.

(56) References Cited

OTHER PUBLICATIONS

Berger et al. (Nov. 25, 2014) "Enhancing the functional maturity of induced pluripotent stem cell-derived human hepatocytes by controlled presentation of cell-cell interactions in vitro" Hepatology, 61(4), 1370-1381. (Year: 2014).*

Zinchenko YS et al. Contribution of Non-parenchymal Cells to the Performance of Micropatterned Hepatocytes. Tissue Engineering. 2006;12(8):2241-2251.

Zinchenko YS et al. Hepatocyte and Kupffer Cells Co-cultured on Micropatterned Surfaces to Optimize Hepatocyte Function. Tissue Engineering. 2006;12(4):751-761.

Morin O, Normand C. Long-Term Maintenance of Hepatocyte Functional Activity in Co-Culture: Requirements for Sinusoidal Endothelial Cells and Dexamethasone. Journal of Cellular Physiology. 1986;129(1):103-110.

Gregory PG et al. The Effect of Coculture with Nonparenchymal Cells on Porcine Hepatocyte Function. Cell Transplantation. 2001; 10:731-738.

Nahmias Y et al. Endothelium-Mediated Hepatocyte Recruitment in the Establishment of Liver-Like Tissue in vitro. Tissue Engineering. vol. 12, No. 6, Jul. 19, 2006, pp. 1627-1638.

Kostadinova R et al. A long-term three dimensional liver co-culture system for improved prediction of clinically relevant drug-induced hepatotoxicity. Toxicology and Applied Pharmacology, 268 (2013) 1-16.

Bhatia et al. Effect of cell-cell interations in preservation of cellular phenotype: cocultivation of hepatocytes and nonparenchymal cells. FASEB J. Nov. 1999;13(14):1883-900.

Bi et al. Use of Cryopreserved Human Hepatocytes in Sandwich Culture to Measure Hepatobiliary Transport. Drug Metab Dispos. Sep. 2006;34(9):1658-65.

International Search Report and Written Opinion, PCT/US2016/045719, dated Oct. 24, 2016.

Khetani SR et al. Toxicological Sciences, Scholarone—Manuscripts: The Use of Micropatterned Co-cultures to Detect Compounds that Cause Drug Induced Liver Injury in Human. ToxSci Advance Access. Nov. 14, 2012.

Khetani SR, Bhatia SN. Microscale culture of human liver cells for drug development. *Nature Biotechnology* 2008; vol. 26, No. 1: pp. 120-126.

Lin C, Shi J, Moore A, Khetani SR. Prediction of Drug Clearance and Drug-Drug Interactions in Microscale Cultures of Human Hepatocytes. Drug Metabolism and Disposition: the biological fate of chemicals. Oct. 2015; DOI: 10.1124/dmd.115.066027.

March S, Hui EE, Underhill GH, Khetani S, Bhatia SN. Microenvironmental Regulation of the Sinusoidal Endothelial Cell Phenotype in vitro. Hepatology. Sep. 2009; 50(3):920-928.

Nagamoto et al. The promotion of hepatic maturation of human pluripotent stem cells in 3D co-culture using type I collagen and Swiss 3T3 cell sheets. Biomaterials, Jun. 2012;33(18):4526-34.

Wang WW, Khetani SR, Krzyzewski S, Duignan DB, Obach RS. Assessment of a Micropatterned Hepatocyte Coculture System to Generate Major Human Excretory and Circulating Drug Metabolites. Drug Metabolism and Disposition. Oct. 2010; DOI: 10.1124/dmd.110.034876.

Liu et al. Hepatocyte cocultures with endothelial cells and fibroblasts on micropatterned fibrous mats to promote liver-specific functions and capillary formation capabilities. Biomacromolecules. Feb. 18, 2014; vol. 15, No. 3: 1044-1054.

Torisawa et al. Transwells with Microstamped Membranes Produce Micropatterned Two-Dimensional and Three-Dimensional Co-Cultures. Tissue Engineering, Part C, vol. 17, No. 1, Jan. 2011 (published online Aug. 25, 2010).

Ware BR, Berger DR, Khetani SR. Prediction of Drug-Induced Liver Injury in Micropatterned Co-cultures Containing iPSC-Derived Human Hepatocytes. Toxicological Sciences, Feb. 2015, 1-11.

Hino H et al. A Long-Term Culture of Human Hepatocytes which Show a High Growth Potential and Express Their Differentiated Phenotypes. Biochemical and Biophysical Research Communications 256 (1999) 184-191.

* cited by examiner

FIG. 3A
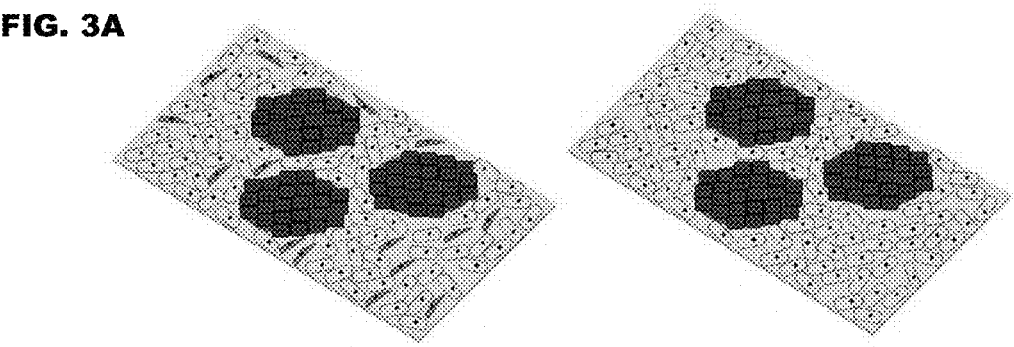
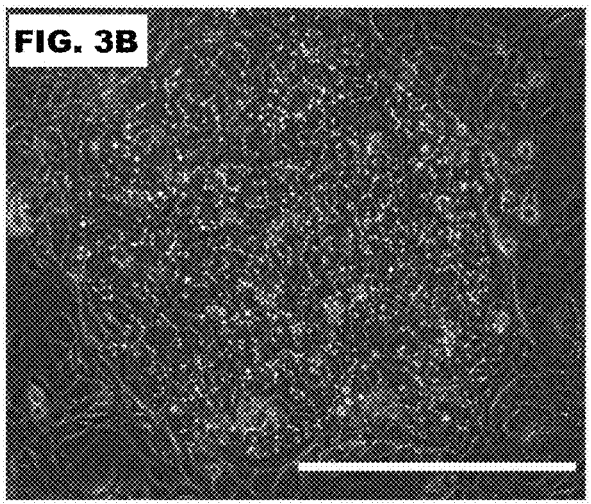
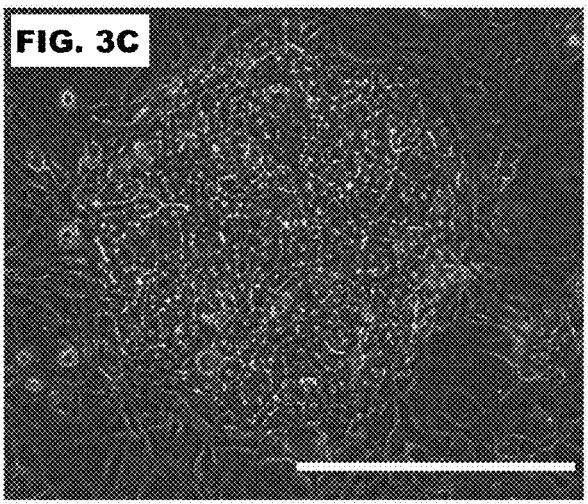
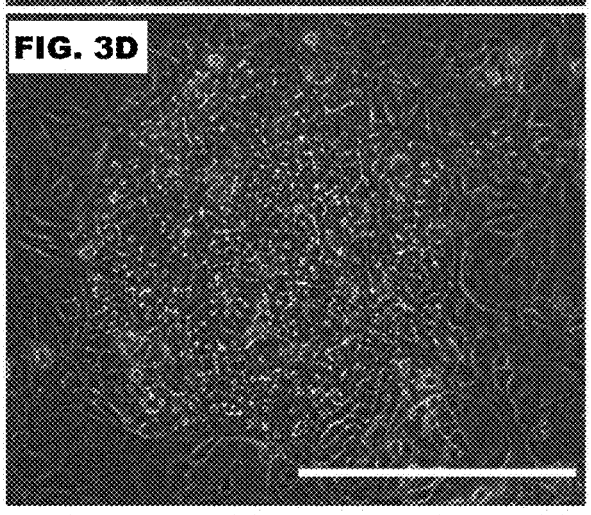
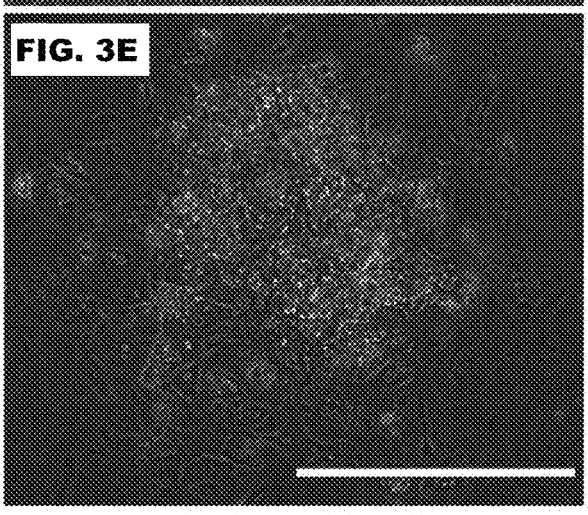

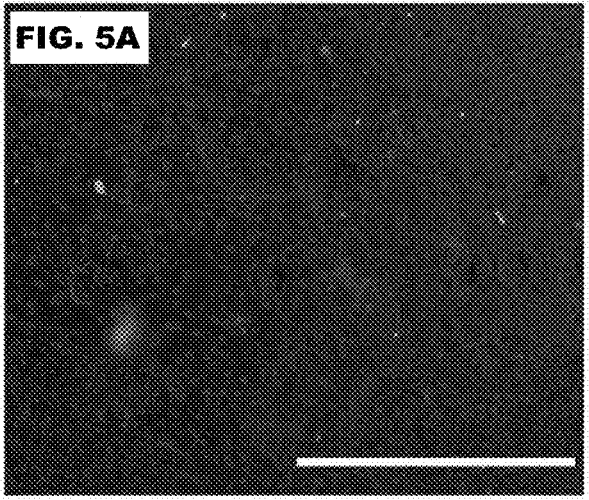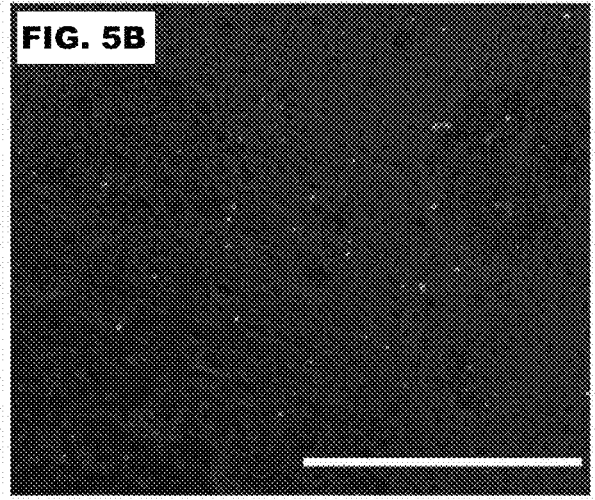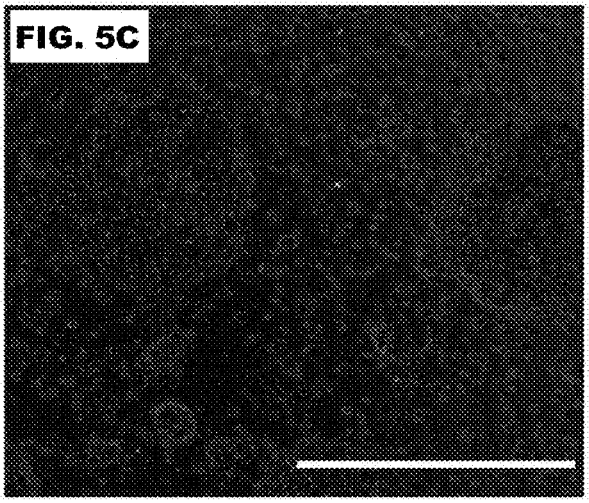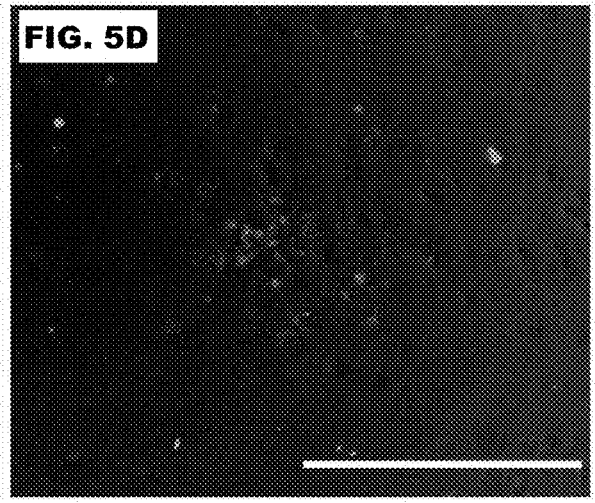

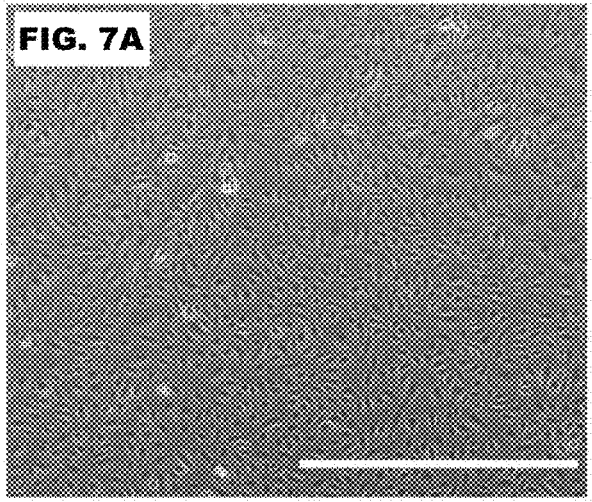
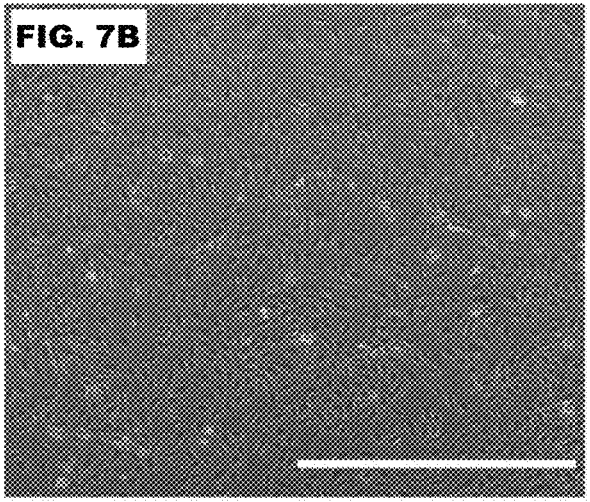
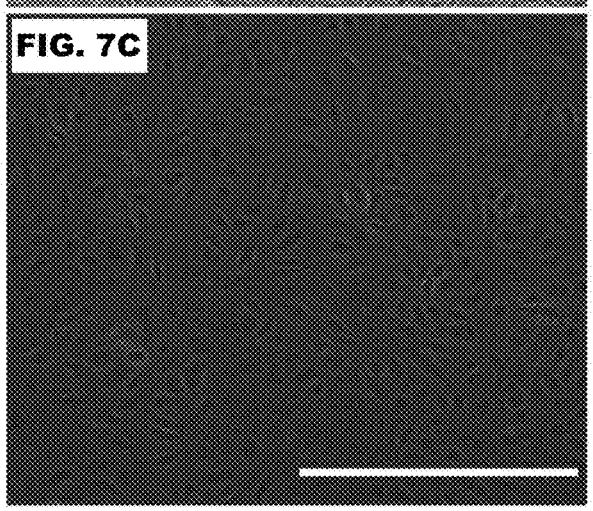
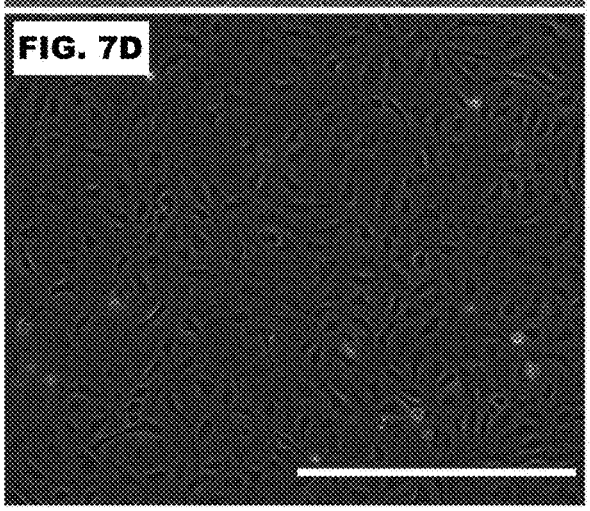

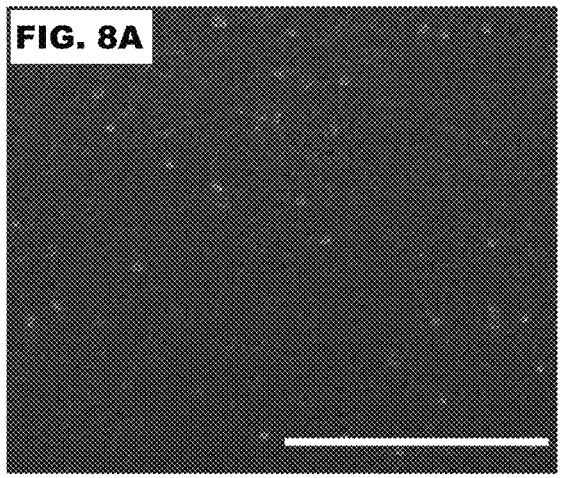
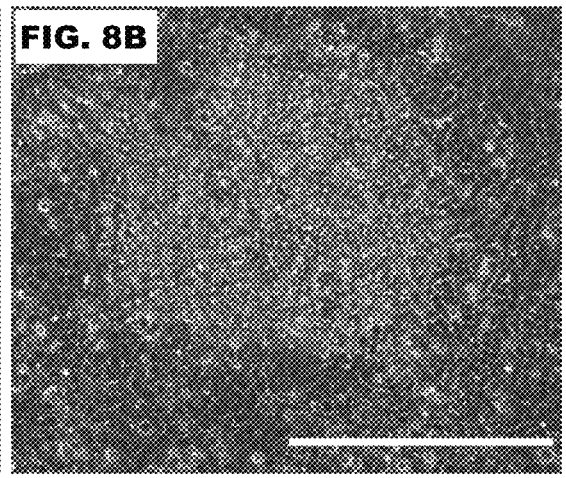
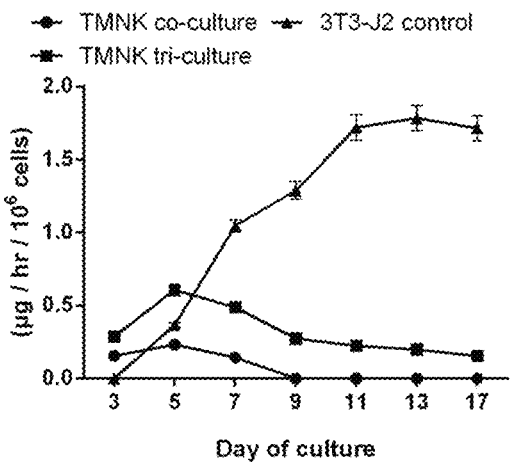
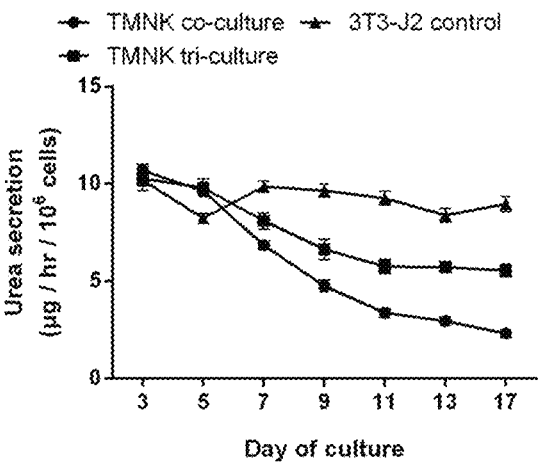
FIG. 8C
FIG. 8D

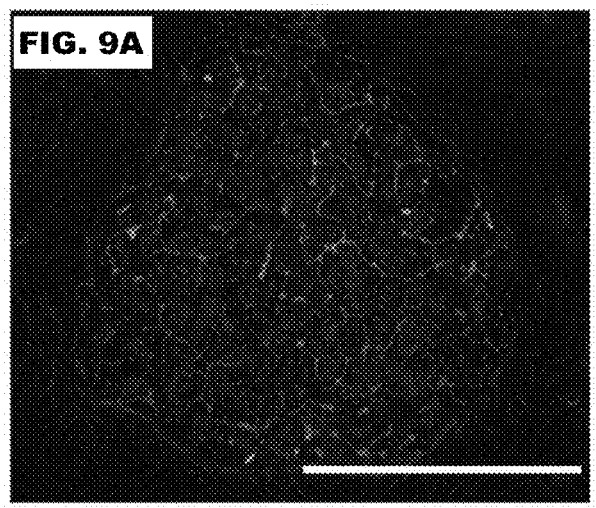
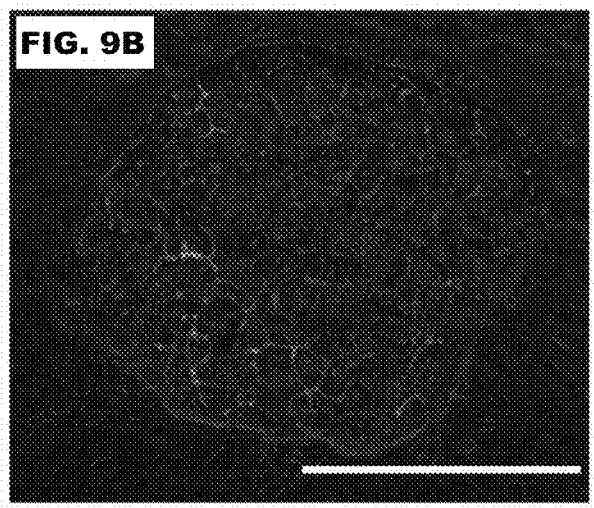
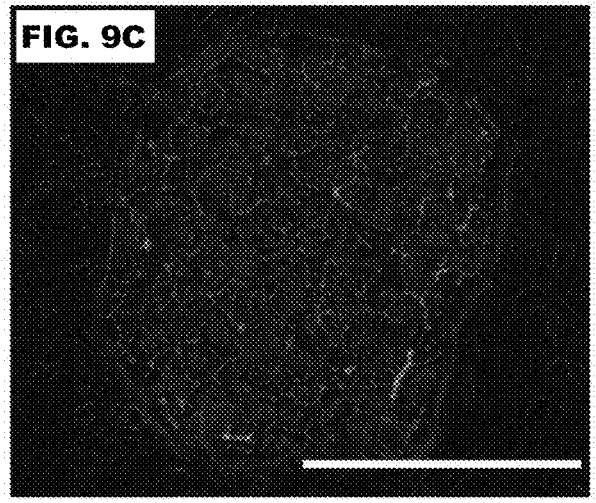
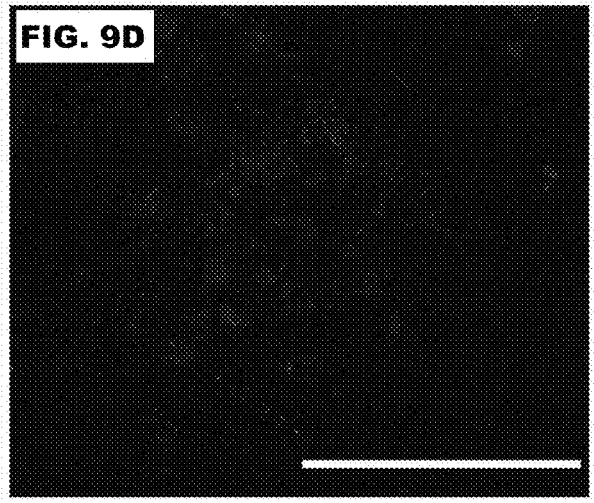

ENGINEERED PLATFORMS TO STABILIZE BOTH HEPATOCYTES AND ENDOTHELIAL CELLS IN VITRO

CROSS REFERENCE TO RELATED APPLICATIONS

This application claims the benefit of U.S. Provisional Application No. 62/201,166, filed Aug. 5, 2015, the disclosure of which is hereby incorporated by reference in its entirety.

GOVERNMENTAL RIGHTS

This invention was made with government support under CBET-1351909 awarded by the National Science Foundation and 1R03EB019184-01 awarded by the National Institutes of Health. The government has certain rights in the invention.

SEQUENCE LISTING

A Sequence Listing submitted in computer readable form (CRF) is hereby incorporated by reference. The CRF file is named 065620-587926_ST25.txt, was created on Aug. 31, 2020, and contains 57 kilobytes.

FIELD OF THE INVENTION

The disclosure relates to in vitro cultures of human hepatocytes, and in particular co-cultures systems including human hepatocytes, non-parenchymal cells, and human endothelial cells, and the use of the co-cultures in developing and screening drugs.

BACKGROUND OF THE INVENTION

The human liver consists of complex interactions between hepatocytes (the main liver cell type), extracellular matrix proteins, soluble factors, and multiple types of non-parenchymal cells. Among these non-parenchymal cells, liver sinusoidal endothelial cells (LSECs) are the most common, comprising about 16% of the total liver cell mass and 70% of all non-parenchymal cells. LSECs act as a barrier between hepatocytes and blood flowing through the liver sinusoid. Other important functions of LSECs include filtering nutrients from the blood, secreting various biochemicals, and contributing to regeneration after liver injury. Upon hepatic injury, LSECs have been shown to have a significantly increased production of the cytokine HGF (hepatocyte growth factor), thereby contributing to liver regeneration. In hepatic fibrosis (an imbalance between the production and degradation of extracellular matrix proteins), LSECs tend to lose their fenestrations (150-175 nm openings that act as a dynamic filter for fluids, solutes, and particles traveling between the sinusoidal blood and hepatocytes). This in turn leads to the secretion of the cytokine IL-33, which activates hepatic stellate cells and further promotes fibrosis. In severe cases, hepatic fibrosis could lead to cirrhosis, an advanced stage of fibrosis that could ultimately lead to hepatocellular carcinoma, the third most common cause of cancer-related deaths. Furthermore, some drugs such as dacarbazine, monocrotaline, and clomiphene citrate are known to cause toxicity specific to LSECs rather than hepatocytes.

Accordingly, co-cultures of human hepatocytes and LSECs can potentially be useful as a model of the early stages of human liver fibrosis and/or drug toxicity.

SUMMARY OF THE INVENTION

In one aspect, the present disclosure provides a composition comprising a population of human hepatocytes, at least one non-parenchymal cell population, and a population of human endothelial cells in co-culture in vitro. The composition may further comprise fibronectin. The composition comprising fibronectin may further comprise a culture substrate wherein the fibronectin is disposed on the culture substrate. The composition may further comprise a layer of material comprising at least one extracellular matrix protein. The layer of material may comprise collagen. The layer of material may comprise a gelatinous protein mixture. The hepatocytes may be disposed in a micropattern on the culture substrate. The micropattern may comprise a predetermined two-dimensional pattern of multiple microdots, the micropattern defined by a microdot diameter and an edge-to-edge spacing between each of any two neighboring microdots. The microdot may have a diameter of 10 μm to 1000 μm. The edge-to-edge spacing between each microdot may be about 700 μm to about 1300 μm. The composition may further comprise a cell adhesion molecule applied to the culture substrate at the microdots, wherein the cell adhesion molecule is a material to which the hepatocytes selectively adhere relative to inter-microdot space. The cell adhesion molecule may be selected from the group consisting of collagen, fibronectin, vitronectin, laminin, Arg-Gly-Asp (RGD) peptide, Tyr-Ile-Gly-Ser-Arg (YIGSR) peptide (SEQ ID NO:1), glycosaminoglycans, hyaluronic acid, integrins, ICAMs, selectins, cadherins and cell surface protein-specific antibodies. The non-parenchymal cell population and population of human endothelial cells may selectively occupy the inter-microdot space. The inter-microdot space may be backfilled with a substance comprising the fibronectin. The inter-microdot space may be backfilled with a substance further comprising at least one extracellular matrix. The extracellular matrix may be selected from collagen and a gelatinous protein mixture. The population of human endothelial cells may be cultured on a layer of material comprising at least one extracellular matrix protein that is disposed on the population of human hepatocytes and at least one non-parenchymal cell population. The population of hepatocytes and the at least one non-parenchymal cell population may be maintained in vitro for at least 7 days, at least 9 days, at least 15 days, at least 21 days, or at least 27 days. The human endothelial cells may be primary human endothelial cells. The primary human endothelial cells may be liver endothelial cells. The primary human endothelial cells may be selected from primary liver sinusoidal endothelial cells (LSECs) and human umbilical vein endothelial cells (HUVECs). The human endothelial cells may be an immortalized human-liver endothelial cell line. The immortalized human-liver endothelial cell line may be TMNK endothelial cell line. The human endothelial cells may be obtained from one or more human donors suffering from a disorder of the liver. The human hepatocytes may be primary human hepatocytes. The human hepatocytes may be derived from pluripotent stems cells. The human hepatocytes may be derived from induced pluripotent human stem cells. The human hepatocytes may be obtained from one or more human donors suffering from a disorder of the liver. The non-parenchymal cells may be obtained from one or more donors suffering from a disorder of the liver. The at least one non-parenchymal cell population may comprise stromal cells. The stromal cells may be selected from fibroblasts, fibroblast-derived cells, macrophages, endothelial cells, pericytes, inflammatory cells, cholangiocytes and other types of stromal cells, and combinations thereof. The stromal cells may comprise embryonic fibroblasts. The stromal cells may comprise murine embryonic fibroblasts. The stromal cells may comprise 3T3-J2 murine embryonic fibroblasts.

In another aspect, the disclosure provides a method of culturing a population of human hepatocytes in vitro comprising: co-culturing the population of human hepatocytes with at least one non-parenchymal cell population, a population of human endothelial cells, and fibronectin. Co-culturing the population of human hepatocytes with at least one non-parenchymal cell population and a population of human endothelial cells may further comprise culturing on a culture substrate, wherein the fibronectin is disposed on the culture substrate. In other aspects, the method may further comprise a layer of material comprising at least one extracellular matrix protein. The layer of material may comprise collagen. The layer of material may comprise a gelatinous protein mixture. The hepatocytes may be disposed in a micropattern on the culture substrate. The micropattern may comprise a predetermined two-dimensional pattern of multiple microdots, the micropattern defined by a microdot diameter and an edge-to-edge spacing between each of any two neighboring microdots. Each microdot may have a diameter of 10 μm to 1000 μm. The edge-to-edge spacing between each microdot may be about 700 μm to about 1300 μm. In other aspects, the method may further comprise a cell adhesion molecule applied to the culture substrate at the microdots, wherein the cell adhesion molecule is a material to which the hepatocytes selectively adhere relative to inter-microdot space. The cell adhesion molecule may be selected from the group consisting of collagen, fibronectin, vitronectin, laminin, Arg-Gly-Asp (RGD) peptide, Tyr-Ile-Gly-Ser-Arg (YIGSR) peptide (SEQ ID NO:1), glycosaminoglycans, hyaluronic acid, integrins, ICAMs, selectins, cadherins and cell surface protein-specific antibodies. The non-parenchymal cell population and population of human endothelial cells may selectively occupy the inter-microdot space. The inter-microdot space may be backfilled with a substance comprising the fibronectin. The inter-microdot space may be backfilled with a substance further comprising at least one extracellular matrix. The extracellular matrix may be selected from collagen and a gelatinous protein mixture. The population of human endothelial cells may be cultured on a layer of material comprising at least one extracellular matrix protein that is disposed on the population of human hepatocytes and at least one non-parenchymal cell population. The population of human hepatocytes with at least one non-parenchymal cell population and a population of human endothelial cells may be maintained in vitro for at least 7 days, at least 9 days, at least 15 days, at least 21 days, or at least 27 days. The human endothelial cells may be primary human endothelial cells. The primary human endothelial cells may be liver endothelial cells. The primary human endothelial cells may be selected from primary liver sinusoidal endothelial cells (LSECs) and human umbilical vein endothelial cells (HUVECs). The human endothelial cells may be an immortalized human-liver endothelial cell line. The immortalized human-liver endothelial cell line may be TMNK endothelial cell line. The human endothelial cells may be obtained from one or more human donors suffering from a disorder of the liver. The human hepatocytes may be primary human hepatocytes. The human hepatocytes may be derived from pluripotent stems cells. The human hepatocytes may be derived from induced pluripotent human stem cells. The human hepatocytes may be obtained from one or more human donors suffering from a disorder of the liver. The non-parenchymal cells may be obtained from one or more donors suffering from a disorder of the liver. The at least one non-parenchymal cell population may comprise stromal cells. The stromal cells may be selected from fibroblasts, fibroblast-derived cells, macrophages, endothelial cells, pericytes, inflammatory cells, cholangiocytes and other types of stromal cells, and combinations thereof. The stromal cells may comprise embryonic fibroblasts. The stromal cells may comprise murine embryonic fibroblasts. The stromal cells may comprise 3T3-J2 murine embryonic fibroblasts.

In still another aspect, the disclosure provides a method of identifying a candidate test compound for use in treating a disorder of the liver, the method comprising: co-culturing the population of human hepatocytes with at least one non-parenchymal cell population, and a population of human endothelial cells in vitro; contacting the co-culture with the test compound; maintaining the co-culture for a time and under conditions sufficient to allow an effect of the test compound on the hepatocytes; and measuring at least one indicator of hepatic function in the hepatocytes to obtain a test measurement, or applying hepatocyte imaging technology (HIAT) to the hepatocytes to obtain a test image; and comparing the test measurement to a control measurement from the hepatocytes before contact with the test compound, or the test image to a control image of the hepatocytes before contact with the test compound, wherein a difference between the test and control is indicative of whether the test compound is a candidate for use in treating a disorder of the liver. The co-culture may be contacted with one or more compounds. The co-culture may be contacted with at least two test compounds. The disorder of the liver may be selected from Type-2 diabetes, metabolic syndrome, non-alcoholic fatty liver disease (NAFLD), non-alcoholic steatohepatitis (NASH), and cardiovascular disease. The disorder of the liver may be an infectious disease. The co-culture may further comprise fibronectin. Co-culturing the population of human hepatocytes with at least one non-parenchymal cell population and a population of human endothelial cells may further comprise culturing on a culture substrate, wherein the fibronectin is disposed on the culture substrate. In other aspects, the method may further comprise a layer of material comprising at least one extracellular matrix protein. The layer of material may comprise collagen. The layer of material may comprise a gelatinous protein mixture. The hepatocytes may be disposed in a micropattern on the culture substrate. The micropattern may comprise a predetermined two-dimensional pattern of multiple microdots, the micropattern defined by a microdot diameter and an edge-to-edge spacing between each of any two neighboring microdots. The non-parenchymal cell population and population of human endothelial cells may selectively occupy the inter-microdot space. The inter-microdot space may be backfilled with a substance comprising the fibronectin. The inter-microdot space may be backfilled with a substance further comprising at least one extracellular matrix. The extracellular matrix may be selected from collagen and a gelatinous protein mixture. The population of human endothelial cells may be cultured on a layer of material comprising at least one extracellular matrix protein that is disposed on the population of human hepatocytes and at least one non-parenchymal cell population. The population of human hepatocytes with at least one non-parenchymal cell population and a population of human endothelial cells may be maintained in vitro for at least 7 days, at least 9 days, at least 15 days, at least 21 days, or at least 27 days. The human endothelial cells may be primary human endothelial cells. The primary human endothelial cells may be liver endothelial cells. The primary human endothelial cells may be selected from primary liver sinusoidal endothelial cells (LSECs) and human umbilical vein endothelial cells (HUVECs). The human endothelial cells may be an immortalized human-liver endothelial cell line. The immortalized human-liver endothelial cell line may be TMNK endothelial cell line. The human endothelial cells may be obtained from one or more human donors suffering from a disorder of the liver. The human hepatocytes may be primary human hepatocytes. The human hepatocytes may be derived from pluripotent stems cells. The human hepatocytes may be derived from induced pluripotent human stem cells. The human hepatocytes may be obtained from one or more human donors suffering from a disorder of the liver. The non-parenchymal cells may be obtained from one or more donors suffering from a disorder of the liver. The at least one non-parenchymal cell population may comprise stromal cells. The stromal cells may be selected from fibroblasts, fibroblast-derived cells, macrophages, endothelial cells, pericytes, inflammatory cells, cholangiocytes and other types of stromal cells, and combinations thereof. The stromal cells may comprise embryonic fibroblasts. The stromal cells may comprise murine embryonic fibroblasts. The stromal cells may comprise 3T3-J2 murine embryonic fibroblasts.

In still yet another aspect, the disclosure provides a method of determining the toxicity of a test compound, the method comprising: co-culturing the population of human hepatocytes with at least one non-parenchymal cell population, and a population of human endothelial cells in vitro; contacting the co-culture with the test compound; maintaining the co-culture for a time and under conditions sufficient to allow an effect of the test compound on the hepatocytes; and measuring at least one indicator of hepatic function in the hepatocytes to obtain a test measurement, or applying hepatocyte imaging technology (HIAT) to the hepatocytes to obtain a test image; and comparing the test measurement to a control measurement from the hepatocytes before contact with the test compound, or the test image to a control image of the hepatocytes before contact with the test compound, wherein a difference between the test and control is indicative of hepatotoxicity of the test compound. The at least one indicator of hepatic function may be selected from the group consisting of albumin production, urea production, ATP production, glutathione production, enzyme activity, lipid accumulation, liver gene expression, and liver protein expression in the hepatocytes. The at least one inducible liver enzyme may be selected from CYP2C9 (luciferin-H), CYP3A4 (luciferin-IPA), a combination of CYP1A1, CYP1A2, CYP2B6, CPY2A6, and CYP2D6 (luciferin ME-EGE), and any combination thereof. The co-culture may further comprise fibronectin. Co-culturing the population of human hepatocytes with at least one non-parenchymal cell population and a population of human endothelial cells may further comprise culturing on a culture substrate, wherein the fibronectin is disposed on the culture substrate. In other aspects, the method may further comprise a layer of material comprising at least one extracellular matrix protein. The layer of material may comprise collagen. The layer of material may comprise a gelatinous protein mixture. The hepatocytes may be disposed in a micropattern on the culture substrate. The micropattern may comprise a predetermined two-dimensional pattern of multiple microdots, the micropattern defined by a microdot diameter and an edge-to-edge spacing between each of any two neighboring microdots. The non-parenchymal cell population and population of human endothelial cells may selectively occupy the inter-microdot space. The inter-microdot space may be backfilled with a substance comprising the fibronectin. The inter-microdot space may be backfilled with a substance further comprising at least one extracellular matrix. The extracellular matrix may be selected from collagen and a gelatinous protein mixture. The population of human endothelial cells may be cultured on a layer of material comprising at least one extracellular matrix protein that is disposed on the population of human hepatocytes and at least one non-parenchymal cell population. The population of human hepatocytes with at least one non-parenchymal cell population and a population of human endothelial cells may be maintained in vitro for at least 7 days, at least 9 days, at least 15 days, at least 21 days, or at least 27 days. The human endothelial cells may be primary human endothelial cells. The primary human endothelial cells may be liver endothelial cells. The primary human endothelial cells may be selected from primary liver sinusoidal endothelial cells (LSECs) and human umbilical vein endothelial cells (HUVECs). The human endothelial cells may be an immortalized human-liver endothelial cell line. The immortalized human-liver endothelial cell line may be TMNK endothelial cell line. The human endothelial cells may be obtained from one or more human donors suffering from a disorder of the liver. The human hepatocytes may be primary human hepatocytes. The human hepatocytes may be derived from pluripotent stems cells. The human hepatocytes may be derived from induced pluripotent human stem cells. The human hepatocytes may be obtained from one or more human donors suffering from a disorder of the liver. The non-parenchymal cells may be obtained from one or more donors suffering from a disorder of the liver. The at least one non-parenchymal cell population may comprise stromal cells. The stromal cells may be selected from fibroblasts, fibroblast-derived cells, macrophages, endothelial cells, pericytes, inflammatory cells, cholangiocytes and other types of stromal cells, and combinations thereof. The stromal cells may comprise embryonic fibroblasts. The stromal cells may comprise murine embryonic fibroblasts. The stromal cells may comprise 3T3-J2 murine embryonic fibroblasts.

In a different aspect, the disclosure provides a method of identifying a candidate test compound for use in treating a disorder of the liver, the method comprising: co-culturing the population of human hepatocytes with at least one non-parenchymal cell population, and a population of human endothelial cells in vitro; contacting the co-culture with the test compound; maintaining the co-culture for a time and under conditions sufficient to allow an effect of the test compound on the endothelial cells; and measuring at least one indicator of endothelial function in the endothelial cells to obtain a test measurement, or applying imaging technology to the endothelial cells to obtain a test image; and comparing the test measurement to a control measurement from the endothelial cells before contact with the test compound, or the test image to a control image of the endothelial cells before contact with the test compound, wherein a difference between the test and control is indicative of whether the test compound is a candidate for use in treating a disorder of the liver. The composition may be contacted with one or more compounds. The composition may be contacted with at least two test compounds. The disorder of the liver may be selected from Type-2 diabetes, metabolic syndrome, non-alcoholic fatty liver disease (NAFLD), non-alcoholic steatohepatitis (NASH), and cardiovascular disease. The disorder of the liver may be an infectious disease. The at least one indicator of endothelial cell function may be selected from the group consisting of a measure of organelle stresses (i.e., reactive oxygen species, mitochondrial membrane potential, markers of endoplasmic reticulum stress, acetylated LDL uptake) via high content imaging, visualization of fenestrae, co-staining with endothelial markers such as factor VIII and CD31, and secretion of factor VIII.

In other aspects, the disclosure provides a method of determining the toxicity of a test compound, the method comprising: co-culturing the population of human hepatocytes with at least one non-parenchymal cell population, and a population of human endothelial cells in vitro; contacting the co-culture with the test compound; maintaining the co-culture for a time and under conditions sufficient to allow an effect of the test compound on the endothelial cells; and measuring at least one indicator of endothelial cell function in the endothelial cells to obtain a test measurement, or applying imaging technology to the endothelial cells to obtain a test image; and comparing the test measurement to a control measurement from the endothelial cells before contact with the test compound, or the test image to a control image of the endothelial cells before contact with the test compound, wherein a difference between the test and control is indicative of toxicity of the test compound. The at least one indicator of endothelial cell function may be selected from the group consisting of a measure of organelle stresses (i.e., reactive oxygen species, mitochondrial membrane potential, markers of endoplasmic reticulum stress, acetylated LDL uptake) via high content imaging, visualization of fenestrae, co-staining with endothelial markers such as factor VIII and CD31, and secretion of factor VIII.

BRIEF DESCRIPTION OF THE FIGURES

The application file contains at least one drawing executed in color. Copies of this patent application publication with color drawing(s) will be provided by the Office upon request and payment of the necessary fee.

(FIG. 1A) Schematic of hepatocyte/endothelia co-cultures (left) and hepatocyte/3T3-J2 co-cultures (right). After a week of culture, (FIG. 1B) co-cultures of hepatocytes with liver sinusoidal endothelial cells (LSECs) and (FIG. 1C) co-cultures of hepatocytes with human umbilical vein endothelial cells (HUVECs), both without 3T3-J2 fibroblasts, show a de-differentiated morphology. As a comparison, (FIG. 1D) co-cultures of hepatocytes with 3T3-J2 fibroblasts maintain a prototypical morphology (i.e., polygonal shape, multi-nucleation) while (FIG. 1E) pure hepatocytes de-differentiated. All scale bars=400 μm.

FIG. 3A, FIG. 3B, FIG. 3C, FIG. 3D and FIG. 3E depict the morphology of hepatocyte/fibroblast/endothelia tri-cultures. (FIG. 3A) Schematic of hepatocyte/fibroblast/endothelia tri-cultures (left) and hepatocyte/3T3-J2 co-cultures (right). After a week of culture, (FIG. 3B) tri-cultures of hepatocytes with 3T3-J2 fibroblasts and sinusoidal endothelial cells (LSECs) and (FIG. 3C) tri-cultures of hepatocytes with 3T3-J2 fibroblasts and human umbilical vein endothelial cells (HUVECs) show a morphology similar to (FIG. 3D) co-cultures of hepatocytes with 3T3-J2 fibroblasts in terms of polygonal shape and multi-nucleation. Contrarily, (FIG. 3E) pure hepatocytes are de-differentiated and spread out. All scale bars=400 μm.

FIG. 5A, FIG. 5B, FIG. 5C and FIG. 5D depict the uptake of acetylated LDL. After 3 weeks in culture, cultures were incubated with fluorescently labeled acetylated LDL (acLDL) and imaged with fluorescence microscopy (see Methods). Both (FIG. 5A) tri-cultures of hepatocytes with 3T3-J2 fibroblasts and sinusoidal endothelial cells (LSECs) and (FIG. 5B) tri-cultures of hepatocytes with 3T3-J2 fibroblasts and human umbilical vein endothelial cells (HUVECs) show more acLDL uptake than (FIG. 5C) co-cultures of hepatocytes with 3T3-J2 fibroblasts. Contrarily, (FIG. 5D) pure hepatocytes show only non-specific acLDL uptake. All scale bars=1000 μm.

FIG. 7A, FIG. 7B, FIG. 7C and FIG. 7D depict the morphology of pure endothelia during expansion. Before culture with hepatocytes, endothelia were expanded in tissue culture flasks as pure cultures. Both (FIG. 7A, FIG. 7C) primary liver sinusoidal endothelial cells (LSECs) and (FIG. 7B, FIG. 7D) human umbilical vein endothelial cells (HUVECs) have a similar, rounded morphology. Endothelia were treated with 0.05% (m/v) trypsin to release cells into suspension, centrifuged, and resuspended in fresh media before co-culturing with hepatocytes. (FIG. 7A-FIG. 7B) Scale bars=1000 μm; (FIG. 7C-FIG. 7D) Scale bars=400 μm.

FIG. 8A, FIG. 8B, FIG. 8C and FIG. 8D depict results from cultures with TMNK endothelial cell line. (FIG. 8A) Pure cultures of the TMNK endothelial cell line before inclusion in co-cultures or tri-cultures with hepatocytes. Scale bar=1000 μm. (FIG. 8B) Tri-culture of hepatocytes with 3T3-J2 fibroblasts and TMNK endothelia after one week in culture. Scale bar=400 μm. (FIG. 8C) Albumin secretions and (FIG. 8D) urea secretions from co-cultures of hepatocytes with TMNK endothelia, tri-cultures of hepatocytes with 3T3-J2 fibroblasts and TMNK endothelia, and co-cultures of hepatocytes with 3T3-J2 fibroblasts. Error bars represent standard deviations (n=3).

FIG. 9A, FIG. 9B, FIG. 9C and FIG. 9D depict results from staining for functional bile canaliculi. After 2 weeks in culture, cultures were washed three times with phenol red-free media, incubated with 2 μg/mL CDF [5-(and 6)-carboxy-2',7'-dichlorofluorescein diacetate; Molecular Probes®, Eugene, OR] for 10 minutes at 37° C., and washed three more times before imaging with fluorescence microscopy (470 nm excitation, 510 nm emission). Both (FIG. 9A) tri-cultures of hepatocytes with 3T3-J2 fibroblasts and sinusoidal endothelial cells (LSECs) and (FIG. 9B) tri-cultures of hepatocytes with 3T3-J2 fibroblasts and human umbilical vein endothelial cells (HUVECs) show more bile canaliculi than (FIG. 9C) co-cultures of hepatocytes with 3T3-J2 fibroblasts. Contrarily, (FIG. 9D) pure hepatocytes show no noticeable bile canaliculi. All scale bars=400 μm.

(FIG. 10A) Schematic of hepatocyte/3T3-J2 co-cultures with a Matrigel® overlay (left) followed by the addition of endothelia (right). After a week of culture, (FIG. 10B) tri-cultures of hepatocytes with 3T3-J2 fibroblasts and sinusoidal endothelial cells (LSECs) in the layered configuration and (FIG. 10C) tri-cultures of hepatocytes with 3T3-J2 fibroblasts and human umbilical vein endothelial cells (HUVECs) in the layered configuration show a morphology similar to (FIG. 10D) co-cultures of hepatocytes with 3T3-J2 fibroblasts and Matrigel® overlay in terms of polygonal shape and multi-nucleation. Contrarily, (FIG. 10E) pure hepatocytes with a Matrigel® overlay are de-differentiated and spread out. All scale bars=400 μm.

DETAILED DESCRIPTION OF THE INVENTION

Figure 1A:
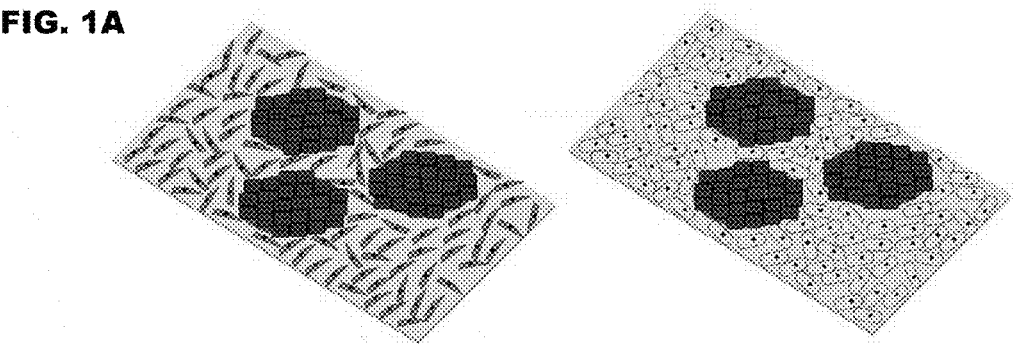
FIG. 1A, FIG. 1B, FIG. 1C, FIG. 1D and FIG. 1E depict the morphology of hepatocyte/endothelia co-cultures.
Figure 1B:
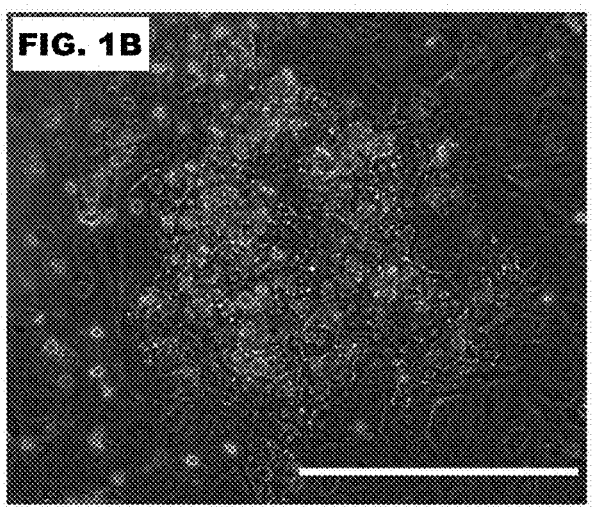
Figure 1C:
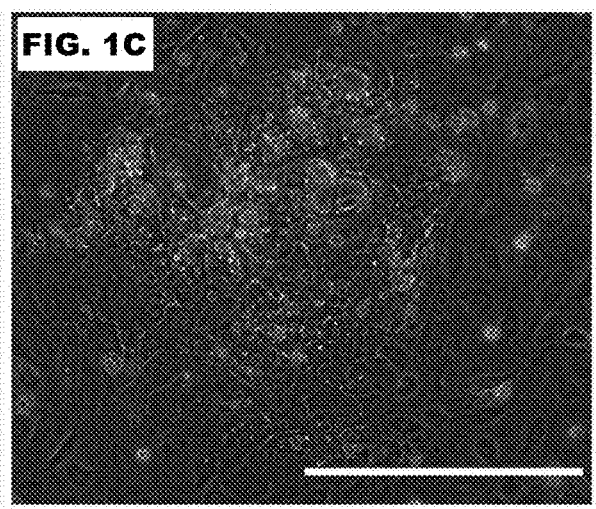
Figure 1D:
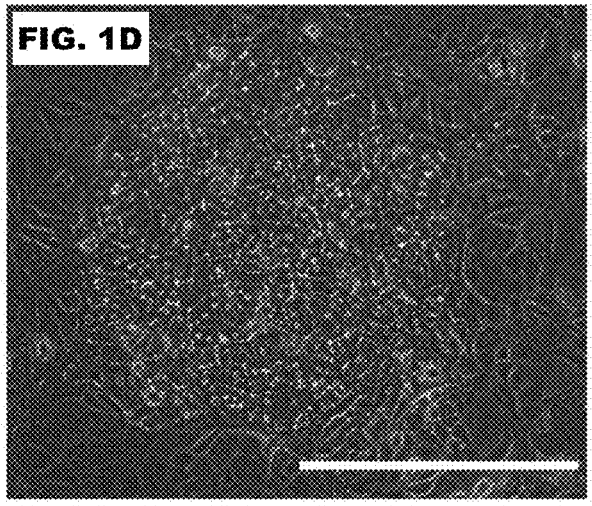

The present disclosure describes the development of an in vitro model based on the interaction between human hepatocytes and human endothelia, whereby a second stromal cell population (murine embryonic 3T3-J2 fibroblasts) is employed to maintain the cultures for a significantly longer time than with conventional cultures of hepatocytes. The disclosed model can be used to screen for drug toxicity (particularly drugs with endothelial-specific and hepatocyte-specific toxicity) as well as study fundamental interactions between hepatocytes and endothelia. The model can be used to examine infectious diseases. For example, as liver sinusoidal endothelial cells (LSECs) contribute to uptake of hepatitis C-like viral particles, the co-cultures disclosed herein may be used to probe hepatitis C infection.

Unless otherwise required by context, singular terms as used herein and in the claims shall include pluralities and plural terms shall include the singular. For example, reference to "a cellular island" includes a plurality of such cellular islands and reference to "the cell" includes reference to one or more cells known to those skilled in the art, and so forth.

The use of "or" means "and/or" unless stated otherwise. Furthermore, the use of the term "including," as well as other forms, such as "includes" and "included," is not limiting. Also, terms such as "element" or "component" encompass both elements and components comprising one unit and elements and components that comprise more than one subunit unless specifically stated otherwise.

Described herein are several definitions. Such definitions are meant to encompass grammatical equivalents.

The term "co-culture" means the growth of more than one distinct cell type in a combined culture. Co-cultures of the present disclosure can include two or more distinct cell types. In some aspects, three or more distinct cell types are included in a co-culture. Co-cultures include, but are not limited to, cultures where two or more cell types are contained in the same container. This includes configurations where one or more of the cell types are contained within a transwell or similar device that is in contact with a container housing one or more cell types.

The term "donor" includes human and other mammalian subjects from which cells such as stem cells, primary endothelial cells, and/or primary hepatocytes may be obtained.

The term "patient" includes human and other mammalian subjects that receive either prophylactic or therapeutic treatment.

The term "population," when referring to a "cell population," "population of . . . cells," and the like, refers to a group of cells of a distinct cell type. The population of cells may contain cells of the same distinct cell type obtained from one or more donors. In other aspects, the population of cells may contain cells of the same distinct type obtained from one or more cell lines.

The term "subject" refers to an animal, including but not limited to a mammal including a human and a non-human primate (for example, a monkey or great ape), a cow, a pig, a cat, a dog, a rat, a mouse, a horse, a goat, a rabbit, a sheep, a hamster, a guinea pig). Preferably, the subject is a human.

I. Co-Cultures of Human Hepatocytes, Non-Parenchymal Cells, and Human Endothelial Cells The present disclosure encompasses a composition comprising a population of human hepatocytes, at least one non-parenchymal cell population, and a population of human endothelial cells in co-culture. The co-cultures as described herein provide a useful in vitro liver model and thus also provide a unique platform for the development and toxicology screening of therapeutic agents, including high-throughput screening of drug candidates for efficacy and toxicity. The co-cultures described herein include, but are not limited to, random co-cultures and micropatterned co-cultures ("MPCC").

The human hepatocytes can be, for example, primary human hepatocytes ("PHHs"), human hepatocytes derived from any human pluripotent stem cells, and an immortalized human hepatocyte cell line. The human hepatocytes may be obtained from a normal human donor or a human donor suffering from a disorder of the liver. Disorders of the liver include, but are not limited to, metabolic disorders such as Type 2 diabetes, metabolic syndrome, non-alcoholic fatty liver disease ("NAFLD"), non-alcoholic steatohepatitis ("NASH"), and cardiovascular disease. Disorders of the liver may also include infectious diseases such as hepatitis B, hepatitis C, hepatitis E, dengue fever, and ebola. The present disclosure encompasses a population of hepatocytes obtained from one or more human donors. A non-limiting, example co-culture is one which includes hepatocytes obtained from one or more human donors suffering from NAFLD or NASH. Another non-limiting, example co-culture is one which includes hepatocytes obtained from one or more normal human donors. Additionally, the human hepatocytes may be derived from any pluripotent stem cells, for example human induced pluripotent stem cells ("iPSC's"), embryonic stem cells ("ESC's"), hepatic resident stem cells (oval cells), and the like. A non-limiting, example co-culture is one which includes hepatocytes derived from human induced pluripotent stem cells such as iCell® Hepatocytes ("iHep" or "iHeps") available from Cellular Dynamics International of Madison, WI. The pluripotent stem cell may be from a normal or a diseased donor.

The non-parenchymal cells may be human or non-human. At least one of the non-parenchymal cell populations may comprise stromal cells, such as but not limited to: fibroblasts, fibroblast-derived cells, macrophages, endothelial cells, pericytes, inflammatory cells, cholangiocytes, and other types of stromal cells, and combinations thereof. Fibroblasts may be, for example, mammalian fibroblasts, such as murine embryonic fibroblasts. Non-limiting example of murine embryonic fibroblasts include 3T3-J2, NIH-3T3, Swiss-3T3, and L1-3T3 murine embryonic fibroblasts. In an aspect, the nonparenchymal cells are 3T3-J2 murine embryonic fibroblasts. A non-limiting, example co-culture is one which includes non-parenchymal cells from normal and diseased patients. Non-parenchymal cells are obtained from one or more donors suffering from a disorder of the liver. It is contemplated that other non-parenchymal cells, both liver and non-liver, and non-parenchymal cells specifically implicated in a disease can be used to provide an in vitro model for drug testing new drugs to treat the disease.

The human endothelial cells can be, for example, primary human endothelial cells, human endothelial cells derived from any human pluripotent stem cells, and an immortalized human endothelial cell line. The human endothelial cells may be obtained from a normal human donor or a human donor suffering from a disorder of the liver. The human endothelial cells may be obtained from the same individual donor as the human hepatocytes. The present disclosure encompasses a population of human endothelial cells obtained from one or more human donors. Non-limiting examples of primary human endothelial cells include human liver endothelial cells, human umbilical vein endothelial cells, human aortic endothelial cells, human coronary artery endothelial cells, human pulmonary artery endothelial cells, human dermal microvascular endothelial cells, human lymphatic endothelial cells, human splenic endothelial cells, human adrenal microvascular endothelial cells, human colonic microvascular endothelial cells, human cardiac microvascular endothelial cells, human adipose microvascular endothelial cells, human esophageal microvascular endothelial cells, human intestinal microvascular endothelial cells, human brain microvascular endothelial cells, and human lung microvascular endothelial cells. In an aspect, the primary human endothelial cells are liver endothelial cells. Specifically, the liver endothelial cells are primary liver sinusoidal endothelial cells (LSECs). In another aspect, the primary human endothelial cells are human umbilical vein endothelial cells (HUVECs). Additionally, the human endothelial cells may be derived from any pluripotent stem cells, for example human induced pluripotent stem cells ("iPSC's"), embryonic stem cells ("ESC's"), hepatic resident stem cells (oval cells), and the like. The pluripotent stem cell may be from a normal or a diseased donor. In another aspect, the human endothelial cells are an immortalized human endothelial cell line. A primary endothelial cell line may be made immortalized by methods known in the art. Specifically, the immortalized human endothelial cell line is an immortalized human-liver endothelial cell line. Non-limiting examples of immortalized human-liver endothelial cell lines include TMNK, HMEC-1, ECV304, and EaHy926 endothelial cell lines.

The co-cultures described herein encompass, but are not limited to, randomly distributed co-cultures of human hepatocytes, non-parenchymal cells, and human endothelial cells, MPCCs, and hybrids of ECM overlay ("sandwich") and MPCCs. Co-culturing methods and techniques in general have been described in the literature. In particular, MPCC co-culturing materials, methods and techniques are described detail in Khetani and Bhatia, NATURE BIOTECHNOLOGY, 2008, 26(1):120-126, incorporated by reference in its entirety. The co-cultures may be contact models where the human hepatocyte population, at least one non-parenchymal cell population, and human endothelial cells are all contained with the same well. Additionally, small molecules for hepatocyte maturation can also be applied in the co-cultures described herein. Small molecule hepatocyte maturation factors can be any from among those described in the literature and as known to those of skill in the art, including for example any of the small molecules described in Shan et al., NATURE CHEM BIOL. 9(8): 514-20 (2013), incorporated by reference in its entirety.

The culture substrate may comprise a glass or elastomeric structure with a suitable culture surface, such as a glass, polystyrene, or silicon slide, or polystyrene dish, slide, or microwells. A biopolymer scaffold may optionally be disposed on the culture substrate to further support and promote cell viability. Biopolymers suitable as scaffold material include, but are not limited to, alginate, chitosan, hyaluronate, fibrous proteins, collagen, silk, and elastin. Alternatively, a scaffold may be disposed on the culture substrate that comprises a hydrogel such as collagens, polyacrylamides, polyelectrolyte multilayers, polydimethylsiloxane. In an aspect, a hard substrate may be used.

Co-cultures of the disclosure may be established as randomly distributed co-cultures of human hepatocytes, non-parenchymal cells, and human endothelial cells. A co-culture of human hepatocytes, non-parenchymal cells, and human endothelial cells may be established by seeding all three cell populations at the same time. In other aspects, a culture of human hepatocytes may be established first, and then non-parenchymal cells added. In some aspects, human endothelial cells are added with the non-parenchymal cells. In other aspects, human endothelial cells are added to the co-culture after the human hepatocytes and non-parenchymal cell co-culture is established.

Figure 2A:
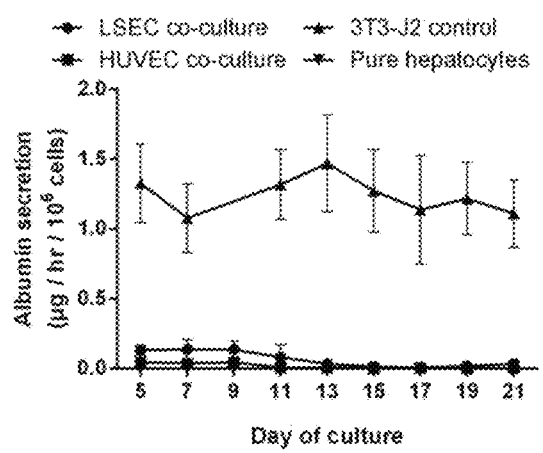
FIG. 2A, FIG. 2B, FIG. 2C and FIG. 2D depict the functionality of hepatocyte/endothelia co-cultures. Co-cultures of hepatocytes with either liver sinusoidal endothelial cells (LSECs) or human umbilical vein endothelial cells (HUVECs) were evaluated for (FIG. 2A) albumin secretions, (FIG. 2B) urea secretions, (FIG. 2C) CYP3A4 activity, and (FIG. 2D) CYP2A6 activity. Co-cultures of hepatocytes with 3T3-J2 fibroblasts and pure hepatocytes were also included for comparison. Error bars represent standard deviations (n=3).

Alternatively, as illustrated in part in FIG. 1A and FIG. 2A, the co-cultures may be established according to a micropattern established on the culture surface (MPCC). Micropatterning is not required to create co-culture models; however, micropatterning allows for clear demarcation of the hepatocyte islands. The micropattern may comprise for example a predetermined two-dimensional pattern of multiple microdots ("islands") of the hepatocytes, wherein each microdot has approximately the same microdot diameter and each of any two neighboring microdots shares approximately the same edge-to-edge spacing. While the microdot diameters and microdot spacing may be varied and do vary for cultures with different cell types, it has been found that for hepatocytes, the micropattern may be characterized by microdots each having a diameter of about 500 μm to about 700 µm, and a center-to-center spacing between each microdot of at least about 1000 µm to at least about 1300 µm, including at least about 1100 µm and at least about 1200 µm. In some aspects the micropattern may be characterized by microdots each having a diameter of about 500 µm, and an edge-to-edge spacing between each microdot of at least about 700 µm. A micropattern having the foregoing characteristics has been found to result in co-cultures of hepatocytes that remain viable and show evidence of mature phenotype retention for several days and weeks, including up to at least about 8 days, at least about 28 days, and at least 35 days. (U.S. Patent Publication No. 2015/0240203, incorporated by reference in its entirety.)

In various aspects, each microdot may have a diameter of 10 µm to 100 µm, a diameter of 50 µm to 150 µm, a diameter of 100 µm to 200 µm, a diameter of 150 µm to 250 µm, a diameter of 200 µm to 300 µm, a diameter of 250 µm to 350 µm, a diameter of 300 µm to 400 µm, a diameter of 350 µm to 450 µm, a diameter of 400 µm to 500 µm, a diameter of 450 µm to 550 µm, a diameter of 500 µm to 600 µm, a diameter of 550 µm to 650 µm, a diameter of 600 µm to 700 µm, a diameter of 650 µm to 750 µm, a diameter of 700 µm to 800 µm, a diameter of 750 µm to 850 µm, a diameter of 800 µm to 900 µm, a diameter of 850 µm to 950 µm, and a diameter of 900 µm to 1000 µm.

In various aspects, the microdots may have an edge-to-edge spacing of 200 µm to 300 µm, an edge-to-edge spacing of 250 µm to 350 µm, an edge-to-edge spacing of 300 µm to 400 µm, an edge-to-edge spacing of 350 µm to 450 µm, an edge-to-edge spacing of 400 µm to 500 µm, an edge-to-edge spacing of 450 µm to 550 µm, an edge-to-edge spacing of 500 µm to 600 µm, an edge-to-edge spacing of 550 µm to 650 µm, an edge-to-edge spacing of 600 µm to 700 µm, an edge-to-edge spacing of 650 µm to 750 µm, an edge-to-edge spacing of 700 µm to 800 µm, an edge-to-edge spacing of 750 µm to 850 µm, an edge-to-edge spacing of 800 µm to 900 µm, an edge-to-edge spacing of 850 µm to 950 µm, an edge-to-edge spacing of 900 µm to 1000 µm, an edge-to-edge spacing of 950 µm to 1050 µm, an edge-to-edge spacing of 1000 µm to 1100 µm, an edge-to-edge spacing of 1050 µm to 1150 µm, an edge-to-edge spacing of 1100 µm to 1200 µm, an edge-to-edge spacing of 1150 µm to 1250 µm, and an edge-to-edge spacing of 1200 µm to 1300 µm.

To establish the micropattern, a cell adhesion molecule may be applied to the culture substrate at the microdots, using for example a PDMS stencil. The cell adhesion molecule is any molecule to which the hepatocytes selectively adhere relative to inter-microdot space, such as collagen, fibronectin, vitronectin, laminin, extracellular matrix proteins, Arg-Gly-Asp (RGD) peptide, Tyr-Ile-Gly-Ser-Arg (YIGSR) peptide (SEQ ID NO:1), glycosaminoglycans, hyaluronic acid, integrins, ICAMs, selectins, cadherins, cell surface protein-specific antibodies, any combination thereof, and any composition composed substantially of purified extracellular matrix protein, or mixtures of extracellular matrix proteins. Suitable extracellular matrix can be provided for example by ECM derived directly from mammalian liver, such as porcine or human liver. In one micropatterned hepatocyte co-culture, the cell adhesion molecule is for example any of the many extracellular matrix protein products available from a variety of commercial suppliers. In another micropatterned hepatocyte co-culture, the cell adhesion molecule is, for example, a commercially available collagen, such as rat tail collagen.

The hepatocytes are seeded onto the culture substrate and allowed to attach. The hepatocytes may be allowed to attach for about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, or about 16 hours. In an aspect, the hepatocytes are allowed to attach for about 4 hours to about 5 hours.

Following seeding of the hepatocytes onto the micropattern, the non-parenchymal cell population and population of human endothelial cells may be seeded onto the culture surface to occupy the inter-microdot space which is not occupied by the hepatocytes. In an aspect, following seeding of the hepatocytes onto the micropattern, fibronectin is added to the culture. In another aspect, following seeding of the hepatocytes onto the micropattern, fibronectin is added to the culture prior to addition of non-parenchymal cells and human endothelial cells. The fibronectin occupies the inter-microdot space and/or the microdot. Accordingly, the inter-microdot space is backfilled with fibronectin. The fibronectin may be added at the same time as the non-parenchymal cell population and human endothelial cell population. Alternatively, the fibronectin may be added about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, or about 24 hours prior to addition of the non-parenchymal cell population and human endothelial cell population. In an aspect, the fibronectin may be added about 12 to about 18 hours prior to addition of the non-parenchymal cell population and human endothelial cell population. The human endothelial cells may be seeded onto the culture surface with the non-parenchymal cell population. Alternatively, the human endothelial cells may be seeded after a co-culture of hepatocytes and non-parenchymal cells has been established.

Fibronectin can also be added to other types of co-cultures, such as randomly distributed co-cultures. In an aspect, following seeding of the hepatocytes, fibronectin is added to the culture prior to addition of non-parenchymal cells and human endothelial cells. The fibronectin may be added about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, or about 24 hours prior to addition of the non-parenchymal cell population and human endothelial cell population. In an aspect, the fibronectin may be added about 12 to about 18 hours prior to addition of the non-parenchymal cell population and human endothelial cell population. In another aspect, the fibronectin may be added at the same time as the non-parenchymal cell population and human endothelial cell population. The human endothelial cells may be seeded onto the culture surface with the non-parenchymal cell population. Alternatively, the human endothelial cells may be seeded after a co-culture of hepatocytes and non-parenchymal cells has been established.

In some aspects, an overlay may be also used. The overlay may be disposed on a co-culture of human hepatocytes and non-parenchymal cells. The overlay may be disposed on a co-culture of human hepatocytes, non-parenchymal cells, and human endothelial cells. Overlays may also be used to enhance hepatic functions. The overlay may be used to restrict human endothelial cells by embedding them into two layers of gel. The co-cultures can be a random co-culture or a MPCC.

Figure 10A:
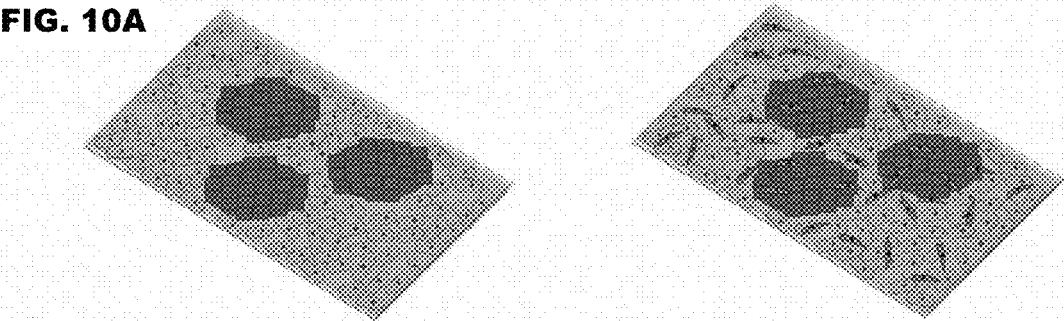
FIG. 10A, FIG. 10B, FIG. 10C, FIG. 10D and FIG. 10E depict the morphology of hepatocyte/fibroblast/endothelia layered tri-cultures.

In another aspect, as illustrated in FIG. 10A, once the hepatocyte and non-parenchymal cell co-culture has been established, the hepatocyte and non-parenchymal cell co-culture can be overlaid with a layer of material comprising at least one extracellular matrix protein and human endothelial cells cultured on top of the layer. Accordingly, a population of human endothelial cells is cultured on a layer of material comprising at least one extracellular matrix protein that is disposed on the population of human hepatocytes and non-parenchymal cells. The layer of material may be a gel. The layer of material or gel may be a biopolymer scaffold. Biopolymers suitable as scaffold material include, but are not limited to, alginate, chitosan, hyaluronate, fibrous proteins, collagen, silk and elastin and gelatinous protein mixtures. In an aspect, the layer of material comprises collagen. The layer of material may contain more than one type of collagen (by way of a non-limiting example, collagen I and collagen IV). In another aspect, the layer of material comprises a gelatinous protein mixture. Matrigel® (Corning Life Sciences) is a commercially available gelatinous protein mixture secreted by Engelbreth-Holm-Swarm (EHS) mouse sarcoma cells. A gelatinous extracellular protein mixture may comprise, but is not limited to, collagens and laminins. It should be understood that any gelatinous protein mixture that mimics the extracellular environment found in biological tissues can also be used as the overlay. Additionally, hydrogels may also be used as the overlay. The hepatocyte and non-parenchymal cell co-culture can be a random co-culture or a MPCC. The layer of material may also comprise fibronectin.

The human endothelial cells may be seeded about 1 or more hours after the human hepatocyte and non-parenchymal cell co-culture is established, about 2 or more hours after the co-culture is established, about 3 or more hours after the co-culture is established, about 4 or more hours after the co-culture is established, about 5 or more hours after the co-culture is established, about 6 or more hours after the co-culture is established, about 7 or more hours after the co-culture is established, about 8 or more hours after the co-culture is established, about nine or more hours after the co-culture is established, about 10 or more hours after the co-culture is established, about 11 or more hours after the co-culture is established, about 12 or more hours after the co-culture is established, about 13 or more hours after the co-culture is established, about 14 or more hours after the co-culture is established, about 15 or more hours after the co-culture is established, about 16 or more hours after the co-culture is established, about 17 or more hours after the co-culture is established, about 18 or more hours after the co-culture is established, about 19 or more hours after the co-culture is established, about 20 or more hours after the co-culture is established, about 21 or more hours after the co-culture is established, about 22 or more hours after the co-culture is established, about 23 or more hours after the co-culture is established, or about 24 or more hours after the co-culture is established. In some aspects, the human endothelial cells may be seeded about one or more days after the co-culture is established, about two or more days after the co-culture is established, about three or more days after the co-culture is established, or about four or more days after the co-culture is established.

The human hepatocyte:human endothelial cells may be seeded at a ratio of about 5:1. In some aspects, the human hepatocyte:human endothelial cells may seeded at a ratio of about 10:1, about 9:1, about 8:1, about 7:1, about 6:1, about 5:1, about 4:1, about 3:1, about 2:1, or about 1:1. In other aspects, the human hepatocyte:human endothelial cells may seeded at a ratio of about 1:10, about 1:9, about 1:8, about 1:7, about 1:6, about 1:5, about 1:4, about 1:3, or about 1:2.

The co-cultures described herein may be maintained in vitro for at least 7 days, at least 8 days, at least 9 days, at least 10 days, at least 11 days, at least 12 days, at least 13 days, at least 14 days, at least 15 days, at least 16 days, at least 17 days, at least 18 days, at least 19 days, at least 20 days, at least 21 days, at least 22 days, at least 23 days, at least 24 days, at least 25 days, at least 26 days, at least 27 days, at least 28 days, at least 29 days, at least 30 days, at least 31 days, or more than 31 days.

The co-cultures described herein can be prepared using a culture medium starting with a base of, for example, Dulbecco's modified Eagle's medium (DMEM) or William's E base. The culture medium may be supplemented with various components known to facilitate growth of cells, specifically hepatocytes. In an aspect, the culture medium further comprises glucose, fetal bovine serum (FBS), insulin, an insulin-transferrin-selenium (ITS) mixture, glucagon, hydrocortisone, a buffer such as HEPES, dexamethasone, an antibiotic or antibiotic mixture such as penicillin-streptomycin, and/or growth factors. The culture medium may comprise high amount of glucose. Further, the culture medium may comprise about 5% to about 10% FBS. Additionally, the culture medium may comprise about 0.5 U/ml insulin. The culture medium may further comprise about 1% ITS. Still further, the culture medium may comprise about 5 ng/ml to about 10 ng/ml glucagon. The culture medium may also comprise about 1% to about 5% of a buffer such as HEPES. Additionally, the culture medium may comprise about 100 nm dexamethasone. Also, the culture medium may comprise about 7.5 μg/ml hydrocortisone. Furthermore, the culture medium may comprise about 1% of an antibiotic or antibiotic mixture such as penicillin-streptomycin. The culture medium may also comprise a growth factor such as VEGF and FGF2. In an aspect, the culture medium comprises VEGF.

The present disclosure also provides a kit for determining the effect of a test agent on hepatocytes. A kit may comprise for example: a population of human hepatocytes, at least one non-parenchymal cell population, and a population of human endothelial cells, for preparing one or more MPCC's as disclosed herein. In one aspect, the hepatocytes may be obtained from one or more human donors suffering a disorder of the liver. The kit may further comprise a culture medium as described herein, and/or additional materials or reagents for testing various biological activities of the cells in culture. For example, the kit may contain separately packaged amounts of a glucose-free medium, pyruvate, lactate, glucose, insulin, glucagon, dexamethasone, metformin, a stain or dye such as but not limited to a fluorimetric dye, a lipid dye such as Nile red, and/or a cellular stain for glycogen such as PAS stain. The kit may further comprise one or more culture substrates such as a glass, silicon, or polystyrene slide or culture well, and an amount of a cell adhesion molecule. The cell adhesion molecule may be disposed according to a micropattern on the culture substrate as described herein above. Alternatively, the kit may provide an amount of the cell adhesion molecule and a PDMS stencil which can be used together to establish a micropattern as described herein on the culture substrate.

The kit may further comprise a reporter molecule or label capable of generating a signal indicative of a level of a cellular activity of interest in the hepatocytes, such as but not limited a vital dye, a lipid dye, a colorimetric agent, or a bioluminescent marker. The kit may include a detectable label such as a fluorophore, a radioactive moiety, an enzyme, a chromophore, a chemiluminescent label, or the like, and/or reagents for carrying out detectable labeling. The labels and/or reporter molecules, any calibrators and/or controls can be provided in separate containers or pre-dispensed into an appropriate assay format, for example, into microtiter plates.

It is contemplated for example that one or more of the presently disclosed co-cultures can be provided in the form of a kit with one or more containers such as vials or bottles, with each container containing a separate population of cells and/or reagents and washing reagents employed in an assay. The kit can comprise at least one container for conducting the assay, and/or a buffer, such as an assay buffer or a wash buffer, either one of which can be provided as a concentrated solution, a substrate solution for the detectable or a stop solution. The kit may comprise all components, e.g., reagents, standards, buffers, diluents, etc., which are necessary to perform the assay. The kit may contain instructions for determining the presence or amount of any metabolite, biomarker, label, or reporter of interest in the co-culture, in paper form or computer-readable form, such as a disk, CD, DVD, or the like, and/or may be made available online.

Optionally, the kit includes quality control components (for example, sensitivity panels, calibrators, and positive controls). Preparation of quality control reagents is well-known in the art and is described on insert sheets for a variety of immunodiagnostic products. Sensitivity panel members optionally are used to establish assay performance characteristics, and further optionally are useful indicators of the integrity of the immunoassay kit reagents, and the standardization of assays.

The kit can also optionally include other reagents required to conduct a diagnostic assay or facilitate quality control evaluations, such as buffers, salts, enzymes, enzyme cofactors, enzyme substrates, detection reagents, and the like. Other components, such as buffers and solutions for the isolation and/or treatment of a test sample (e.g., pretreatment reagents), also can be included in the kit. The kit can additionally include one or more other controls. One or more of the components of the kit can be lyophilized, in which case the kit can further comprise reagents suitable for the reconstitution of the lyophilized components.

The various components of the kit optionally are provided in suitable containers as necessary, e.g., a microtiter plate. Where appropriate, the kit optionally also can contain reaction vessels, mixing vessels, and other components that facilitate the preparation of reagents or the test sample. The kit can also include one or more instruments for assisting with obtaining a test sample, such as a syringe, pipette, forceps, measured spoon, or the like.

II. Uses

The hepatocyte co-cultures as described herein may be used in various methods, such as but not limited to drug discovery and drug screening. Such co-culture systems can be used to develop and screen candidate therapeutic agents for treating any hepatic disease or disorder, or for screening the toxicity of candidate therapeutic agents for treating any other disease or disorder. In an aspect, the hepatic disease or disorder is an infectious disease such as hepatitis B, hepatitis C, hepatitis E, dengue fever, and ebola. For example, co-cultures as described herein show the effects of human endothelial cells on hepatocytes and provide for a model of in vitro prediction of drug induced liver toxicity, and establish a new direction in in vitro models of the liver.

A candidate therapeutic agent (also referred to as a "drug candidate" or "test compound") may be a small molecule, a peptide, a polypeptide, an oligonucleotide, a polynucleotide, or an antibody.

Any of the methods may involve determining a baseline or control value, for example, of any indicator of liver function such as gluconeogenesis, glycolysis, glycogen storage, enzyme activity, albumin secretion, urea production, gene expression, inducible liver enzyme activity and the like, in the hepatocytes in co-culture before administering a dosage of a candidate therapeutic agent or other test agent, and comparing this with a value or level after the exposure and noting any significant change (i.e., greater than the typical margin of experimental error in repeat measurements of the same sample, expressed as one standard deviation from the mean of such measurements) over the control. In a non-limiting example, at least one indicator of hepatic function can be a measure of albumin production, urea production, ATP production, glutathione production, enzyme activity, lipid accumulation, liver gene expression, liver protein expression, or inducible liver enzyme activity in the hepatocytes.

In another aspect, any of the methods may involve determining a baseline or control value, for example, of any indicator of endothelial cell function such as a measure of organelle stresses (i.e., reactive oxygen species, mitochondrial membrane potential, markers of endoplasmic reticulum stress, acetylated LDL uptake) via high content imaging, visualization of fenestrae, co-staining with endothelial markers such as factor VIII and CD31, secretion of factor VIII, and the like, in the endothelial cells in co-culture before administering a dosage of a candidate therapeutic agent or other test agent, and comparing this with a value or level after the exposure and noting any significant change (i.e., greater than the typical margin of experimental error in repeat measurements of the same sample, expressed as one standard deviation from the mean of such measurements) over the control. In a non-limiting example, at least one indicator of endothelial cell function can be a measure of organelle stresses (i.e., reactive oxygen species, mitochondrial membrane potential, markers of endoplasmic reticulum stress, acetylated LDL uptake) via high content imaging, visualization of fenestrae, co-staining with endothelial markers such as factor VIII and CD31, and secretion of factor VIII.

(a) Screening Assays

The present disclosure provides an in vitro model of diseases or disorders of the liver which can be utilized in various methods for identifying and screening of potential therapeutic agents, and for drug development. Disorders of the liver include, but are not limited to, metabolic disorders such as Type 2 diabetes, metabolic syndrome, non-alcoholic fatty liver disease ("NAFLD"), and non-alcoholic steatohepatitis ("NASH"). In an aspect, the hepatic disease or disorder is an infectious disease, such as hepatitis B, hepatitis C, hepatitis E, dengue fever, and ebola.

For example, the compositions of the present disclosure may be used in vitro to screen a wide variety of compounds, such as small molecules, antibodies, peptides, polypeptides, nucleic acid-based agents and the like, to identify therapeutic agents having a therapeutic effect on liver function in any disease or disorder of the liver, and/or to assess the toxicity of any such therapeutic agent before clinical implementation. For example, following contact of a co-culture with a candidate therapeutic agent, various cellular functions in the hepatocytes and/or human endothelial cells may be assessed by examining gene expression, albumin production, urea production, cytochrome P450 (CYP) metabolic activity or any inducible liver enzyme activity, organelle stress, cell surface markers, secreted factors, uptake and secretion of liver-specific products, and response to hepatotoxins, by detecting and/or measuring level of a protein, metabolite, reporter molecule, label, or gene expression level such as through gene fluorescence in the cell or in the culture media. In non-limiting example, at least one indicator of hepatic function can be, for example, albumin production, urea production, ATP production, glutathione production, enzyme activity, lipid accumulation, liver gene expression, or liver protein expression in the hepatocytes. In a non-limiting example, at least one indicator of endothelial cell function can be a measure of organelle stresses (i.e., reactive oxygen species, mitochondrial membrane potential, markers of endoplasmic reticulum stress, acetylated LDL uptake) via high content imaging, visualization of fenestrae using electron microscopy, co-staining with endothelial markers such as factor VIII and CD31, and/or secretion of factor VIII.

Gluconeogenesis and other liver functions such as albumin secretion, urea production, and glycolysis and glycogen storage may be monitored in the presence and absence of one or more stimuli, test agent, or candidate therapeutic agent. For example, hepatocytes in co-culture as described herein may be tested for any one or more of albumin secretion, urea production, ATP production, lipid accumulation, induction of inducible liver (e.g., CYP) enzyme levels, gluconeogenesis, glycolysis and glycogen storage in the presence and absence of varying levels of candidate therapeutic agents. In any method involving measurement of one or more inducible liver enzymes, such enzymes include, in non-limiting example, CYP enzymes such as CYP2C9 (luciferin-H), CYP3A4 (luciferin-IPA), CYP1A1, CYP1A2, CYP2B6, CYP2A6, and CYP2D6 (luciferin ME-EGE), all CYP450 enzymes such as CYP2C8, CYP2C19, CYP2E1, and phase II enzymes such as UGTs, SULTs and NATs, and any combination thereof.

Levels of biomarkers such as for example specific metabolites may also be used in screening assays for agents. This may also be accomplished using standard cytological and/or histological techniques including the use of immunocytochemical techniques employing stains that recognize specific cellular components such as lipids, or antibodies that specifically bind to biomarkers with antigenic activity. For example, co-cultures of the present disclosure may be exposed to a test agent or candidate therapeutic agents. After incubation, the co-cultures may be examined for change in biomarker production as an indication of the efficacy of the test substance. Varying concentrations of a candidate therapeutic agent may be tested as known in the art to derive a dose-response curve.

(b) Target Validation

The compositions of the disclosure can be used in drug development for specific target identification and target validation. The disclosed co-cultures are useful for identifying targets and predicting the role of one or more biomolecules in liver function in a disease or disorder of the liver. A "disease or disorder of the liver" is any medical condition having a negative effect on any liver function. Non-limiting examples of liver diseases and disorders include cirrhosis, diabetes, fibrosis, any chronic hepatitis (including but not limited to A, B, C, D, and E), non-alcoholic fatty liver disease ("NAFLD"), alcoholic fatty liver, tumors of the liver such as hepatic carcinoma, and genetic disorders such as alpha-1-anti-trypsin deficiency.

For example, the cultures and systems may be used to identify proteins playing a potential role in fibrosis of the liver, or those playing a potential role in diabetic processes or diabetic liver pathways. Identified proteins may be modulated (e.g., up-regulated or down-regulated) in the co-cultures described herein, and processes and pathways related to diabetes may be assayed following modulation.

The co-cultures and systems are also useful for validating the predicted role of one or more biomolecules in liver function in a disease or disorder of the liver. For example, proteins identified in preliminary studies (e.g., studies of primary hepatocytes in conventional culture systems or cryogenically preserved hepatocytes, studies in other liver models, differential expression studies, etc.) as playing a potential role in disease processes or disease pathways can be tested in a composition as described herein to confirm the potential role. Proteins identified from preliminary studies, for example proteins suspected to play a role in diseased or disordered liver function, may be modulated (e.g., up-regulated or down-regulated) in the co-cultures described herein, and processes and pathways related to the disease or disorder may be assayed following modulation. For example, candidate proteins can be "knocked out/down" using gene knockout or suppression techniques, for example, using various genomic editing techniques, or the introduction of RNA interference (RNAi) agents. Inhibition of liver pathways may be tested following down-regulation and candidate proteins thought to be important in disease or disordered liver function may be thus validated.

Any method using the co-cultures as disclosed herein may comprise initially preparing or otherwise obtaining a co-culture of hepatocytes, non-parenchymal cells, and human endothelial cells as described herein. In one aspect, a stable, growing co-culture is established as described herein above. In one aspect, the present disclosure provides a method of determining the efficacy of a candidate therapeutic agent for treating a disease or disorder of the liver. The candidate therapeutic agent may be a small molecule, a peptide, a polypeptide, an oligonucleotide, a polynucleotide, or an antibody.

The co-culture is exposed to varying concentrations of the candidate therapeutic agent. The amount of the candidate therapeutic agent may be, according to knowledge available to those of skill in the art, an amount representing a proposed dose or range of proposed doses in a clinical population. The time over which the hepatocytes in the co-culture are exposed to the candidate therapeutic agent may be, according to knowledge available to those of skill in the art, a period of days, weeks, or months representing time course of exposure in a clinical population. After incubation with the agent, the culture is examined to determine impact of the agent if any on one or more target biomolecules or pathways identified as potentially involved in liver function in a disease or disorder of the liver, as described above. Once a testing range is established, varying concentrations of the agent can be tested to determine therapeutically effective amount of the test compound.

As noted above, the human hepatocytes and/or human endothelial cells can be obtained or derived from human donors. In further aspects, human hepatocytes and/or human endothelial cells can be derived from stem cells obtained from one or more human donors. In another aspect, the human hepatocytes and/or human endothelial cells can be obtained from one or more human donors suffering from a disease or disorder of the liver. Alternatively, the human hepatocytes and/or human endothelial cells can be derived from stem cells obtained from one or more human donors suffering from a disease or disorder of the liver.

By way of example, human hepatocytes and/or human endothelial cells can be obtained from one or more human donors suffering from a metabolic disorder of the liver. The methods therefore encompass, for example, a method for testing a candidate therapeutic agent for treating a disorder of the liver, including maintaining a co-culture as described herein for a time and under conditions sufficient to allow glucose production by the hepatocytes; and determining a level of glucose production by the hepatocytes, wherein the level of glucose production relative to the level of glucose production in a population of control hepatocytes is indicative of the efficacy of the test compound as an therapeutic agent for treating the disorder of the liver. The method may further comprise, prior to determining the level of glucose production by the hepatocytes: depleting the co-culture of glycogen in glucose-free medium for a period of at least about 12 hours; contacting the co-culture with at least one substrate of a gluconeogenesis enzyme; and maintaining the co-culture for a period of at least about 12 hours under conditions sufficient for glucose production in the hepatocytes to occur. The co-culture may be maintained for a period of at least about 24 hours, or at least 48 hours under conditions sufficient for glucose production in the hepatocytes to occur. The at least one substrate of a gluconeogenesis enzyme may be for example lactate or pyruvate.

It should be understood that the present disclosure encompasses methods of identifying any test agent useful for modulating a biological activity of interest in a hepatocyte or human endothelial cells, in which a co-culture as disclosed herein is contacted with the test agent; the co-culture is maintained for a time and under conditions sufficient for the hepatocytes to generate a signal indicative of the biological activity; and a signal generated by the hepatocytes in the presence of the test agent is detected, wherein the signal relative to a signal generated in a control hepatocyte in a control co-culture is indicative of an effect on the biological activity of interest in the hepatocytes. The signal indicative of the biological activity of interest may be for example a protein expression level or a protein secretion level. The biological activity of interest may be glucose metabolism. The biological activity of interest may be albumin secretion or urea synthesis.

(c) Toxicity Studies

In addition to the above-described uses of the cultures and/or systems of the disclosure in screening for therapeutic agents for treating a disease or disorder of the liver, the co-cultures may also be used in toxicology studies to determine the hepatotoxicity of an agent identified as a potential therapeutic agent. Toxicology studies may be performed on co-cultures featuring hepatocytes and/or human endothelial cells from human donors suffering from a disease or disorder of the liver, as described herein, which may be contrasted with comparable studies in cells from a different source. The co-cultures described herein may be used in vitro to test a variety of potential therapeutic compounds for hepatotoxicity. Any of the screening methods described herein above may further comprise determining the toxicity of the agent by measuring in the hepatocytes and/or human endothelial cells at least one cell signal indicative of cell toxicity.

Toxicity results may be assessed for example by observation of any of the following: a change in albumin and/or urea production, induction of any inducible liver enzyme such as cytochrome P450 (CYP) enzymes, cellular necrosis, loss of membrane integrity, cell lysis, decrease in cell viability, apoptosis, mitochondrial membrane potential, mitochondrial DNA, ER stress, organelle stress, change in endothelial cell surface markers, secretion of cell factors, and steatosis, using any one or more of vital staining techniques, ELISA assays, RT-qPCR, immunohistochemistry, imaging, electron microscopy, and the like or by analyzing the cellular content of the culture, e.g., by total cell counts, and differential cell count, by metabolic markers such as MTT and XTT, or by hepatocyte imaging technology (HIAT).

For example, co-cultures as described herein are exposed to varying concentrations of a candidate therapeutic agent. The amount of the candidate therapeutic agent may be, according to knowledge available to those of skill in the art, an amount representing a proposed dose or range of proposed doses in a clinical population. The time over which the hepatocytes and human endothelial cells are exposed to the candidate therapeutic agent may be, according to knowledge available to those of skill in the art, a period of days, weeks, or months representing time course of exposure in a clinical population. After incubation with the agent, the culture is examined to determine the highest tolerated dose, i.e., the concentration of the agent at which the earliest morphological and/or functional abnormalities appear or are detected. Cytotoxicity testing may also be performed using a variety of supravital dyes to assess cell viability in the culture system, using techniques known to those skilled in the art. Once a testing range is established, varying concentrations of the agent can be examined for hepatotoxic effect.

The present disclosure thus provides a method for determining the cellular toxicity of a candidate therapeutic agent or test compound, the method comprising contacting a co-culture as described herein with the test compound; maintaining the co-culture for a time and under conditions sufficient to allow an effect of the test compound on the hepatocytes and/or human endothelial cells; and taking a test measurement and/or otherwise obtaining test data indicative of a negative impact of the test compound on hepatocytes and/or human endothelial cells, which is indicative of toxicity of the test compound. The test measurement can be any measurement which provides an indicator of hepatic cell or human endothelial cells function. In a non-limiting example, at least one indicator of hepatic function can be a measure of albumin production, urea production, ATP production, glutathione production, enzyme activity, lipid accumulation, liver gene expression, liver protein expression, or inducible liver enzyme activity in the hepatocytes. In a non-limiting example, at least one indicator of endothelial cell function can be a measure of organelle stresses (i.e., reactive oxygen species, mitochondrial membrane potential, markers of endoplasmic reticulum stress, acetylated LDL uptake) via high content imaging, visualization of fenestrae using electron microscopy, co-staining with endothelial markers such as factor VIII and CD31, and/or secretion of factor VIII. For example, the test measurement can be a measurement of at least one or any combination of albumin, urea, enzyme activity, lipid accumulation, ATP production, and gene expression. The test measurement can be a measurement of at least one inducible liver (e.g., CYP) enzyme level. Test data may include applying hepatocyte imaging technology (HIAT) to the hepatocytes and/or human endothelial cells to obtain a test image. Test data may include using other imaging technology on the co-cultures, hepatocytes, and/or human endothelial cells to obtain a test image. The test measurement and/or test image is compared to a control measurement or control image from the hepatocytes and/or human endothelial cells before contact with the test compound, and a difference between the test measurement and control measurement, or between test image and control image is indicative of toxicity of the test compound. For example, a relative decrease in albumin and/or urea production in test measurements as compared to control, following exposure of the co-culture to the test compound is indicative of hepatotoxicity.

The present disclosure also provides a method of determining the toxicity arising from a drug interaction. For example, the potential toxicity of an interaction between a first test compound and a second test compound can be examined by contacting a co-culture as described herein with the first and second test compounds; maintaining the co-culture for a time and under conditions sufficient to allow an effect of an interaction between the first and second test compounds on the hepatocytes; and taking a test measurement and/or otherwise obtaining test data as described above, which is indicative of toxicity of the interaction of the first and second test compounds.

The present disclosure also provides a method of determining whether a test compound alleviates hepatic dysfunctions caused by hepatocytes and/or human endothelial cells. For example, the effects of a test compound can be examined by contacting a co-culture as described herein with the test compound; maintaining the co-culture for a time and under conditions sufficient to allow an effect of the test compound on the hepatocytes and human endothelial cells; and taking a test measurement and/or otherwise obtaining test data as described above, which is indicative of effect of test compounds on hepatic function. In some aspects more than one test compound can be examined at one time. For example, two, three, four, five, six, 7, 8, 9, or 10 test compounds can be examined.

Additionally, the present disclosure thus also provides a method for determining the effects of chronically elevated or reduced levels of glucose, fructose and/or fatty acids on the liver and liver function. The method comprises for example contacting a co-culture as described herein with a predetermined amount of one or more metabolites such as glucose, fructose, and or fatty acids, wherein the hepatocytes or human endothelial cells are obtained from one or more human donors suffering from a disorder of the liver; maintaining the co-culture for a time and under conditions sufficient for the hepatocytes to generate a signal indicative of modified cellular function induced by the predetermined amount of one or more metabolites; and detecting the signal generated by hepatocytes in the presence of the one or more metabolites, wherein the signal relative to a signal generated in a control cell subject to the same conditions is indicative of an effect of the amount of the one or more metabolites on the hepatocytes. The signal indicative of an effect on cell function may be a change in transcription, translation or secretion of a protein, cellular necrosis, loss of membrane integrity, cell lysis, decrease in cell viability, apoptosis, mitochondrial membrane potential, mitochondrial DNA, ER stress, and steatosis. The predetermined amount may be an amount which is elevated or reduced relative to a control amount which is representative of an amount of each metabolite which is considered within the range of normal in vivo values for the metabolite. The time over which the hepatocytes are exposed to the elevated or reduced level(s) of metabolite(s) may be, according to knowledge available to those of skill in the art, a period of days, weeks or months representing chronic elevation or reduction of the metabolite in a clinical population.

It should be understood that many other signals of toxicity from the hepatocytes and human endothelial cells can be detected and/or measured and compared to controls to identify and/or quantify toxicity induced by a candidate therapeutic agent, wherein the signal relative to a signal generated in a control co-culture is indicative of a toxic effect of the candidate agent on the hepatocytes and/or human endothelial cells. Such signals include, in non-limiting example, cellular necrosis, loss of membrane integrity, cell lysis, decrease in cell viability, apoptosis, mitochondrial membrane potential, mitochondrial DNA, ER stress, and steatosis, any one of which can be readily measured using techniques and materials known in the art.

(d) Personalized Medicine

It has been found that certain correlations can exist between an individual subject's particular genotype with respect to specific molecular markers, and drug treatment efficacy. Any of the co-cultures and methods described herein can also be used to develop personalized medicine, to determine whether any such correlation exists between a particular genotype and selected drug treatment for a disease or disorder of the liver. For example, co-cultures can be prepared using human hepatocytes and/or human endothelial cells derived from pluripotent stem cells obtained from a variety of donors of different genotypes, and any therapeutic candidate can be tested for efficacy against each genotype to determine whether any one or subset of the tested genotypes fares better or worse with a given therapeutic candidate. Any therapeutic candidate can be tested for effect on any inducible liver enzymes, and/or for a negative interaction with a second therapeutic candidate. Such information considered together with the genotype of an individual patient, can be used by a health care provider to determine a treatment option with the highest likelihood of efficacy for the individual subject, and/or to determine a risk of a negative side effect in the individual subject from a therapeutic candidate.

It will be readily apparent to those skilled in the art that other suitable modifications and adaptations of the methods of the disclosure described herein are obvious and may be made using suitable equivalents without departing from the scope of the disclosure or the embodiments disclosed herein. Having now described the present disclosure in detail, the same will be more clearly understood by reference to the following examples, which are included for purposes of illustration only and are not intended to be limiting of the disclosure.

EXAMPLES

The following examples are included to demonstrate various embodiments of the present disclosure. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1. Engineered Co-Cultures of Primary Human Liver Sinusoidal Endothelial Cells and Hepatocytes On the microscale, the human liver consists of complex interactions between hepatocytes, ECM, soluble factors, and several types of non-parenchymal cells, all in a precisely defined architecture. The liver sinusoidal endothelial cell (LSEC) is the most predominant, comprising about 70% of the non-parenchymal cells in the liver and about 16% of the total liver cell mass. LSECs, along with the ECM-based space of Disse, act as a barrier between hepatocytes and blood flowing through the liver sinusoid. As a major component of the liver sinusoid, LSECs are responsible for filtering nutrients from the blood, secreting various biochemicals, and contributing to regeneration after liver injury via increased production of the cytokine HGF. Clinically, LSECs are associated with key pathophysiologic conditions, including liver fibrosis, drug toxicity, and hepatitis. In the early stages of hepatic fibrosis, LSECs secrete the cytokine IL-33, which activates hepatic stellate cells and further promotes fibrosis. Some drugs, including azathioprine, dacarbazine, and monocrotaline, are known to cause toxicity specific to LSECs rather than hepatocytes. Lastly, in vitro cultures containing LSECs have been shown to readily uptake hepatitis C-like virus particles, whereas cultures lacking LSECs did not.

Co-cultures of primary human hepatocytes (PHHs) and primary LSECs can potentially be useful as a physiologic model of the human liver. A few investigators have created co-cultures in vitro, and they have claimed endothelial cells can support hepatic function relative to pure hepatocyte monolayers. However, these claims are based off of rat hepatocyte co-cultures utilizing human aortic endothelial cells (HAECs) or human umbilical vein endothelial cells (HUVECs). Additional attempts have been made to culture rat hepatocytes with rat LSECs by implementing microfluidic devices or changing the extracellular matrix to which LSECs attach. These culture methods result in relatively low hepatic functions and lack human relevance. In the absence of a stable and physiologically relevant model of PHH functions, it is not possible to ascertain whether a specific stromal cell type, such as LSECs, positively or negatively impacts the human hepatic phenotype.

The hepatic phenotype of both human- and animal-derived hepatocytes is stabilized in vitro via co-culture with stromal cells from multiple sources. Hepatic function and culture longevity was further improved when incorporated into a micropatterned co-culture (MPCC), whereby PHHs were arranged onto collagen domains of empirically optimized dimensions and surrounded by 3T3-J2 murine embryonic fibroblasts. These fibroblasts have been shown to induce the highest functions relative to other 3T3 clones, liver macrophages, and hepatic stellate cells. As a non-liver cell line, 3T3-J2 fibroblasts can stabilize the hepatic phenotype of PHHs independently of liver stromal cells, thereby allowing studies of endothelial cell functions on a stable PHH background. Furthermore, higher throughput biological inquiries and drug toxicity screens are possible since the MPCC platform is amenable to an industry-standard 96-well plate, and high content imaging studies can be performed since the model is a 2D monolayer.

In this study, the hepatic functions of cultures with PHHs and endothelial cells with or without 3T3-J2 murine embryonic fibroblasts were compared.

Methods.

Processing of primary human hepatocytes. Cryopreserved primary human hepatocytes (PHHs) were obtained from commercial vendors permitted to sell products derived from human organs procured in the U.S. by federally designated Organ Procurement Organizations. The HUM4011 donor (26 year-old Caucasian male who died of cardiac arrest) and HUM4055A donor (54 year-old Caucasian female who died of stroke) from Triangle Research Labs (Research Triangle Park, NC) were the PHH donors used in this study. After thawing, PHHs were suspended in seeding media (William's E base (Sigma-Aldrich®, St. Louis, MO) with 1.5% (v/v) HEPES buffer (Corning® Life Sciences, Tewksbury, MA), 1% (v/v) ITS+ Premix (Corning® Life Sciences), 1% (v/v) penicillin/streptomycin (Corning® Life Sciences), 100 nM dexamethasone (Sigma-Aldrich®), and 7 ng/mL glucagon (Sigma-Aldrich®)). Cells were centrifuged at 500 rpm for 10 minutes, resuspended in fresh seeding media, and counted.

Fibroblast culture. Murine embryonic 3T3-J2 fibroblasts were a gift from Howard Green of Harvard Medical School. Cells were cultured at 37° C., 10% $CO_2$ in Dulbecco's Modified Eagle's Medium (DMEM, Corning® Life Sciences) with high glucose, 10% (v/v) bovine calf serum (Life Technologies), and 1% (v/v) penicillin-streptomycin. Fibroblasts were passaged up to 12 times prior to use in MPCCs.

Endothelia culture. Primary liver sinusoidal endothelial cells (LSECs) were a gift from Dr. Hugo Rosen of the University of Colorado-Denver Medical School. Cells were cultured at 37° C., 10% $CO_2$ in Endothelial Cell Medium (ScienCell® Research Laboratories, Carlsbad, CA) on fibronectin-coated (2 µg/cm$^2$) tissue culture polystyrene. A second donor of LSECs was purchased from ScienCell® and used to verify the results. Pooled-donor human umbilical vein endothelial cells (HUVECs) were purchased from Lonza® (Williamsport, PA) and cultured at 37° C., 10% $CO_2$ with EGM™-2 BulletKit™ (Lonza®). Both endothelial cell types were passaged up to six times before use in co-culture.

Establishment of MPCC cultures. Tissue culture polystyrene 24-well plates (Corning® Life Sciences) were coated for 2 hours with 25 µg/mL rat tail collagen-I (Corning® Life Sciences) and rinsed twice with sterile water. After drying, these plates were subjected to polydimethylsiloxane (PDMS) mask-based soft lithography to micropattern circular collagenous islands (500 µm diameter, 1200 µm center-to-center spacing) as previously described (Khetani and Bhatia, *Nat Biotechnol* 2008; 26(1): 120-6, Berger et al., *Hepatology* 2015; 61(4): 1370-81, the disclosures of which are hereby incorporated by reference in their entirety). Cryopreserved PHHs after processing were seeded at a density of 6.67×10$^5$ cells/mL into collagen micropatterned wells (300 µL/well). After allowing 4-5 hours for cellular attachment and spreading onto collagen-coated islands, wells were washed 3× in DMEM base medium to remove unattached cells, leaving ~3×10$^4$ PHHs per well in 24-well format (~90 islands/well). Cultures in the co-planar arrangement were backfilled with fibronectin (2 µg/cm$^2$) before endothelia and 3T3-J2 fibroblasts were seeded 12-18 hours later and allowed to fill the remaining area surrounding the PHH islands. The hepatocyte:endothelial ratio was chosen to match the physiologic ratio of 5 hepatocytes (3×10$^4$ per well) to 1 endothelium (6×10$^3$ per well), and 3T3-J2 fibroblasts were added to bring the total stromal cell count to 9×10$^4$ cells per well. Cultures in the layered configuration were seeded with 9×10$^4$ 3T3-J2 fibroblasts per well 12-18 hours after seeding PHHs to fill in remaining areas, overlaid with 250 µg/mL Matrigel® (Corning® Life Sciences), and then seeded with 6×10$^3$ endothelia per well the following day. Culture supernatants were changed with fresh, serum-containing medium every other day.

Drug dosing studies. After ~1 week of stabilization, cultures were dosed in serum-free culture medium (i.e., i.e., little to no binding of drug to protein) for 6 days, (3 doses that corresponded to standard media changes). Doses up to 100×$C_{max}$ (the maximum plasma concentration) were applied to cultures to parallel doses used in previous studies. The $C_{max}$ values of azathioprine (3.61 µM), dacarbazine (43.91 µM), and monocrotaline (10 µM) were each established in previous literature. The dimethyl sulfoxide (DMSO) concentration that MPCCs were exposed to was kept at 0.1% (v/v) relative to culture medium for all conditions. Vehicle-only controls were maintained at 0.1% (v/v) DMSO to serve as a baseline for comparison. Azathioprine and monocrotaline were purchased from Cayman Chemical® (Ann Arbor, MI), while dacarbazine was purchased from Sigma-Aldrich® (St. Louis, MO).

Hepatic morphological, functionality, and health assessments. The morphology of MPCCs was monitored using an EVOS® FL cell imaging system (Life Technologies) with standard 4×, 10×, and 20× phase contrast objectives. CYP3A4 activity in MPCCs was measured using the luminescence-based luciferin-IPA assay from Promega® (Madison, WI) per manufacturer's instructions. CYP2A6 was evaluated by treating the cultures with 50 μM coumarin for 1 hour and measuring the production of the metabolite 7-hydroxycoumarin. Albumin secretions were assessed with an enzyme-linked immunosorbent assay (ELISA) with horseradish peroxidase detection and 3,3',5,5'-tetramethylbenzidine as the substrate. Urea production was measured via a colorimetric endpoint analysis with diacetylmonoxime, acid, and heat (Stanbio® Labs, Boerne, TX). Endothelia were observed by the uptake of acetylated LDL (acLDL) uptake. Cultures were washed with phenol red-free media, incubated with 20 μg/mL Alexa Fluor®-conjugated acLDL (Life Technologies) for 3 hours at 37° C., and washed five more times before imaging with fluorescence microscopy (470 nm excitation, 510 nm emission).

Gene expression analysis. Messenger RNA was extracted from cultures with the RNeasy® kit (Qiagen®) and homogenized via centrifugation through homogenizing columns (Omega Bio-Tek®, Norcross, GA). Genomic DNA was removed with a 1 hour treatment with DNAse I (New England Biolabs®, Ipswich, MA), and cDNA was synthesized with the High-Capacity cDNA Reverse Transcription Kit (Applied Biosystems®, Foster City, CA). Human-specific primers were chosen to avoid cross-reactivity with the 3T3-J2 fibroblasts, which was verified with pure cultures of 3T3-J2 fibroblasts.

Data analysis. Data processing and visualization were performed using Microsoft® Excel® and GraphPad Prism® (La Jolla, CA). For drug toxicity studies, data were normalized to the appropriate DMSO-only control, and mean and standard deviation values were calculated using three technical replicates for each drug dose administered.

Results.

Sourcing of endothelia. Both primary liver sinusoidal endothelial cells (LSECs) and human umbilical vein endothelial cells (HUVECs) were able to be cultured in vitro (FIG. 7), expanded, and passaged with trypsinization. Both endothelia types maintained a comparable morphology that was clearly distinguishable from the elongated morphology of 3T3-J2 fibroblasts. The cellular morphology of the immortalized LSEC cell-line, TNMK, was also visualized (FIG. 8A).

Figure 1E:
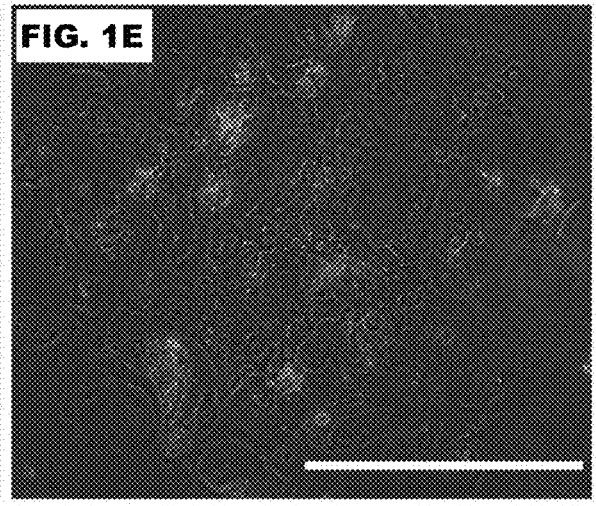

Co-cultures of hepatocytes and endothelia. Co-cultures of hepatocytes and endothelia were compared with co-cultures of hepatocytes and 3T3-J2 fibroblasts as illustrated in FIG. 1. Co-cultures of hepatocytes with liver sinusoidal endothelial cells (LSECs) (FIG. 1B) and co-cultures of hepatocytes with human umbilical vein endothelial cells (HUVECs) (FIG. 1C), both without 3T3-J2 fibroblasts, show a de-differentiated morphology. In contrast, co-cultures of hepatocytes with 3T3-J2 fibroblasts maintain a prototypical morphology (i.e., polygonal shape, multi-nucleation) (FIG. 1D) while pure hepatocytes were de-differentiated (FIG. 1E).

Figure 2B:
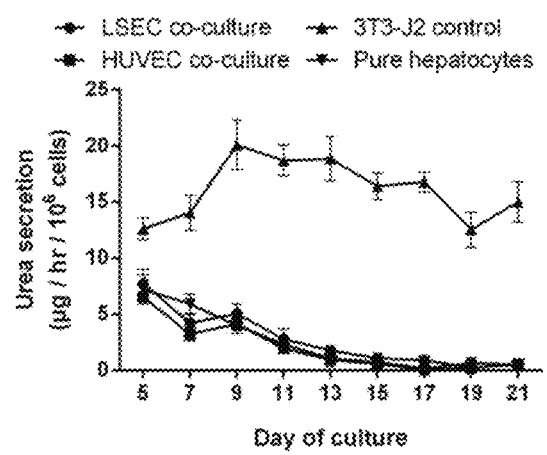
Figure 2C:
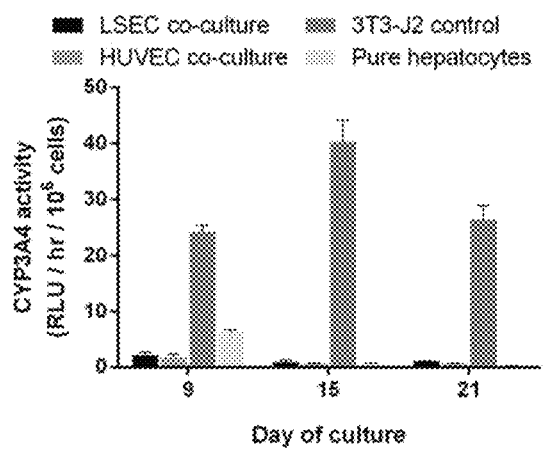
Figure 2D:
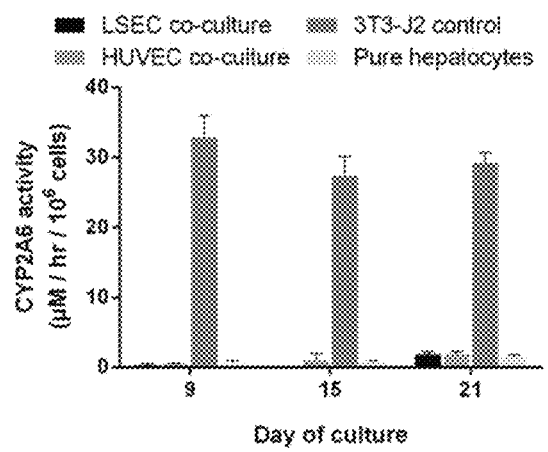

The function of the hepatocyte and endothelia co-cultures was examined by assaying for albumin secretion, urea secretion and CYP3A4 and CYP2A6 activity. Results demonstrated that the co-cultures of hepatocytes and endothelia did not secrete albumin (FIG. 2A) or urea (FIG. 2B). Additionally, little to no activity of CYP3A4 (FIG. 2C) and CYP2A6 (FIG. 2D) was observed in the co-cultures with hepatocytes and endothelia. This trend was also consistent with a variable number of endothelia used in the co-cultures. Ratios from 5 hepatocytes to 1 endothelium (physiologic) to 1 hepatocyte to 4 endothelia (supraphysiologic) all failed to maintain hepatic functions.

Figure 4A:
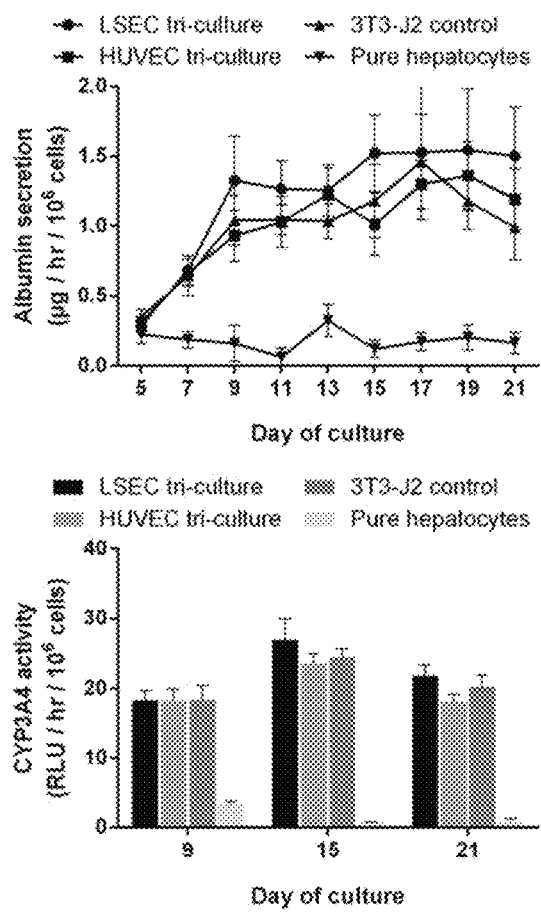
FIG. 4A, FIG. 4B, FIG. 4C and FIG. 4D depict the functionality of hepatocyte/fibroblast/endothelia tri-cultures. Tri-cultures of hepatocytes with 3T3-J2 fibroblasts and either liver sinusoidal endothelial cells (LSECs) or human umbilical vein endothelial cells (HUVECs) were evaluated for (FIG. 4A) albumin secretions, (FIG. 4B) urea secretions, (FIG. 4C) CYP3A4 activity, and (FIG. 4D) CYP2A6 activity. Co-cultures of hepatocytes with 3T3-J2 fibroblasts and pure hepatocytes were also included for comparison. Error bars represent standard deviations (n=3).
Figure 4B:
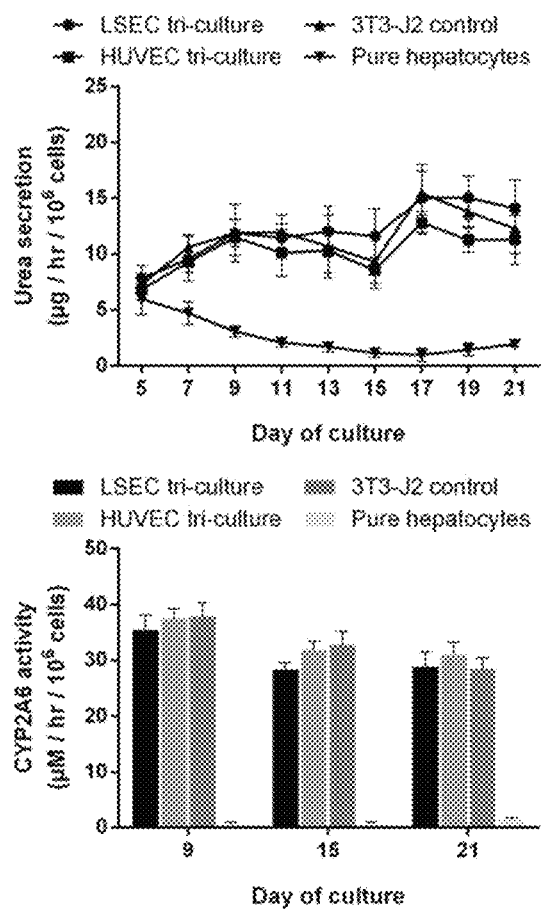
Figure 4C:
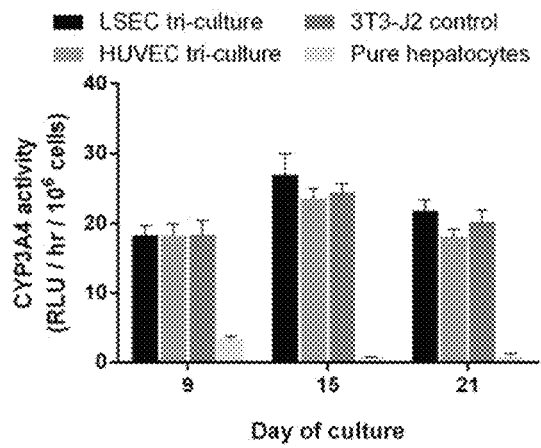
Figure 4D:
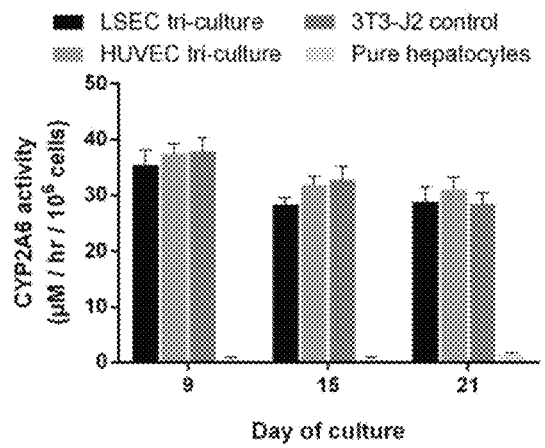

Co-cultures of hepatocytes, endothelia, and fibroblasts. Co-cultures of hepatocytes, endothelia, and fibroblasts were compared with co-cultures of hepatocytes and 3T3-J2 fibroblasts as illustrated in FIG. 3. Co-cultures of hepatocytes with liver sinusoidal endothelial cells (LSECs) (FIG. 3B) and co-cultures of hepatocytes with human umbilical vein endothelial cells (HUVECs) (FIG. 3C), both with 3T3-J2 fibroblasts, show a morphology similar to co-cultures of hepatocytes with 3T3-J2 fibroblasts (FIG. 3D) in terms of polygonal shape multi-nucleation. However, pure hepatocytes were de-differentiated (FIG. 3E). The function of the hepatocyte, endothelia, and fibroblast co-cultures was examined by assaying for albumin secretion, urea secretion and CYP3A4 and CYP2A6 activity. Results demonstrated that the co-cultures of hepatocytes, endothelia, and fibroblasts secreted albumin (FIG. 4A) or urea (FIG. 4B) at levels comparable to co-cultures of hepatocytes and fibroblasts. Additionally, activity of CYP3A4 (FIG. 4C) and CYP2A6 (FIG. 4D) was comparable in the co-cultures with hepatocytes, endothelia, and fibroblasts relative to co-cultures with hepatocytes and fibroblasts.

Similar experiments were conducted with immortalized endothelia cell line, TMNK. Results demonstrated that use of the immortalized cell line resulted in an intermediate phenotype (FIG. 8B). Albumin secretion and urea secretion measured in the co-culture with hepatocytes, TMNK endothelia, and fibroblasts fell in between the co-culture with hepatocytes and fibroblasts and co-culture with hepatocytes and TMNK endothelia cells (FIG. 8C, FIG. 8D).

Endothelia function was evaluated by imaging uptake of acetylated LDL. After 3 weeks in culture, cultures were incubated with fluorescently labeled acetylated LDL (acLDL) and imaged with fluorescence microscopy. Both co-cultures of hepatocytes with 3T3-J2 fibroblasts and sinusoidal endothelial cells (LSECs) (FIG. 5A) and co-cultures of hepatocytes with 3T3-J2 fibroblasts and human umbilical vein endothelial cells (HUVECs) (FIG. 5B) show more acLDL uptake than co-cultures of hepatocytes with 3T3-J2 fibroblasts (FIG. 5C). In contrast, pure hepatocytes show only non-specific acLDL uptake (FIG. 5D).

The co-cultures were also stained for functional bile canaliculi. After 2 weeks in culture, cultures were washed three times with phenol red-free media, incubated with 2 μg/mL CDF [5-(and 6)-carboxy-2',7'-dichlorofluorescein diacetate; Molecular Probes®, Eugene, OR] for 10 minutes at 37° C., and washed three more times before imaging with fluorescence microscopy (470 nm excitation, 510 nm emission). Both cu-cultures of hepatocytes with 3T3-J2 fibroblasts and sinusoidal endothelial cells (LSECs) (FIG. 9A) and co-cultures of hepatocytes with 3T3-J2 fibroblasts and human umbilical vein endothelial cells (HUVECs) (FIG. 9B) show more bile canaliculi than co-cultures of hepatocytes with 3T3-J2 fibroblasts (FIG. 9C). In contrast, pure hepatocytes show no noticeable bile canaliculi (FIG. 9D).

Figure 6A:
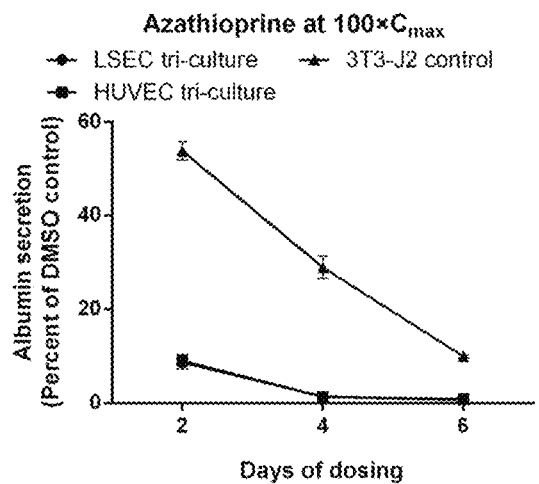
FIG. 6A, FIG. 6B, FIG. 6C and FIG. 6D depict drug toxicity screens in hepatocyte/fibroblast/endothelia tri-cultures. Albumin secretions were compared in tri-cultures of hepatocytes with 3T3-J2 fibroblasts and either liver sinusoidal endothelial cells (LSECs) or human umbilical vein endothelial cells (HUVECs) dosed with (FIG. 6A) azathioprine at $100 \times C_{max}$, (FIG. 6B) azathioprine at $50 \times C_{max}$, (FIG. 6C) dacarbazine at $100 \times C_{max}$, and (FIG. 6D) monocrotaline at $100 \times C_{max}$ for 6 days in serum-free media. Co-cultures of hepatocytes with 3T3-J2 fibroblasts are included for comparison. All data have been normalized to the respective DMSO-only controls. Error bars represent standard deviations (n=3).
Figure 6B:
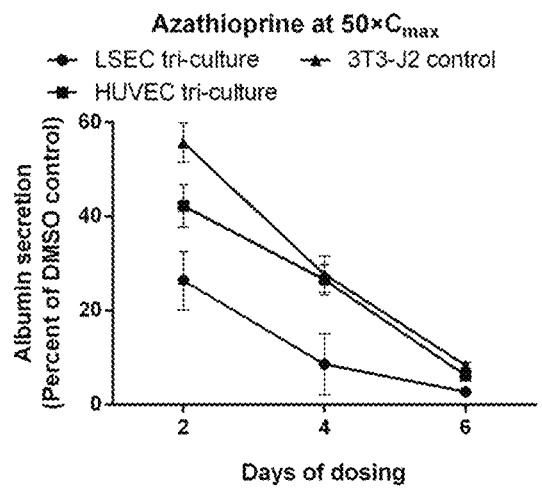
Figure 6C:
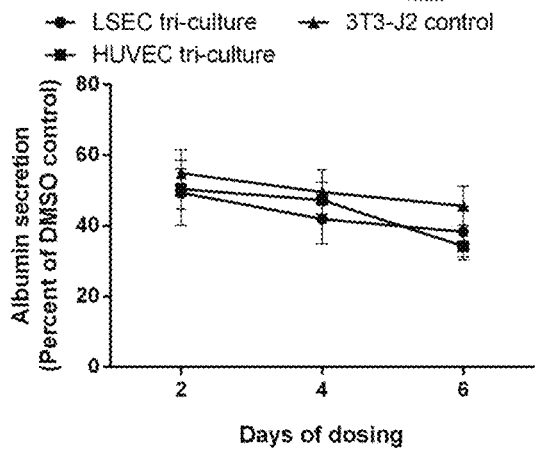
Figure 6D:
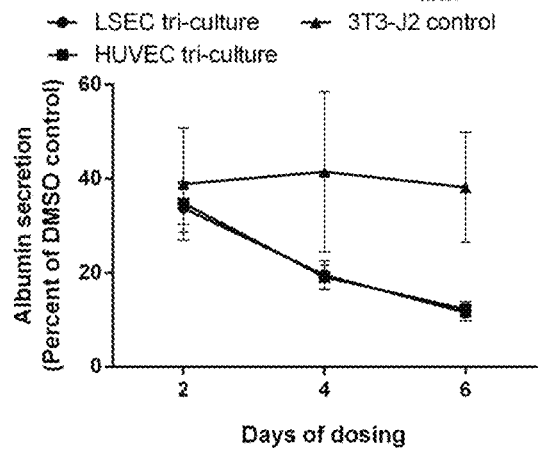

Drug toxicity screens in co-cultures of hepatocytes, endothelia, and fibroblasts. Drug toxicity in co-cultures of hepatocytes, endothelia and fibroblasts was compared to drug toxicity in co-cultures of hepatocytes and fibroblasts. Albumin secretions were compared in co-cultures of hepatocytes with 3T3-J2 fibroblasts and either liver sinusoidal endothelial cells (LSECs) or human umbilical vein endothelial cells (HUVECs) dosed with azathioprine at $100 \times C_{max}$ (FIG. 6A), azathioprine at $50 \times C_{max}$ (FIG. 6B), dacarbazine at $100 \times C_{max}$ (FIG. 6C), and monocrotaline at $100 \times C_{max}$ (FIG. 6D) for 6 days in serum-free media. Co-cultures of hepatocytes with 3T3-J2 fibroblasts were included for comparison. Co-cultures comprising endothelia cells were more responsive to drug toxicity.

Figure 10B:
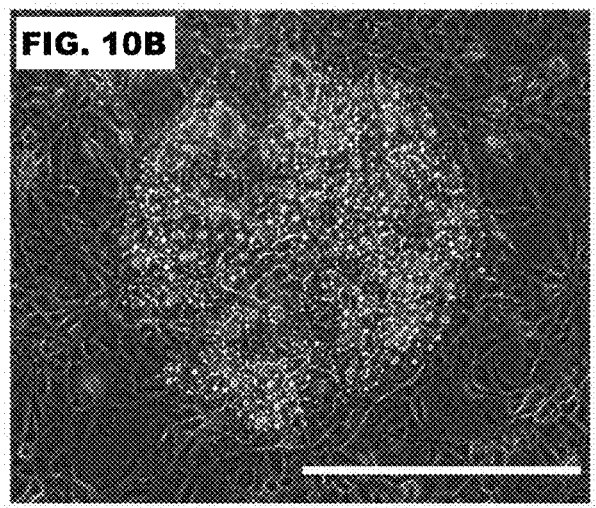
Figure 10C:
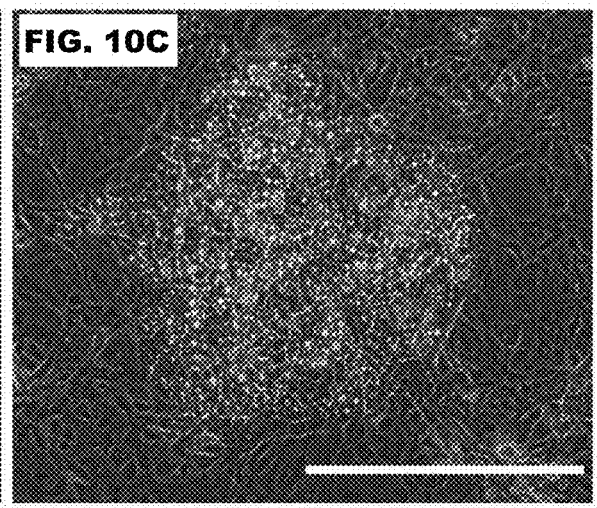
Figure 10D:
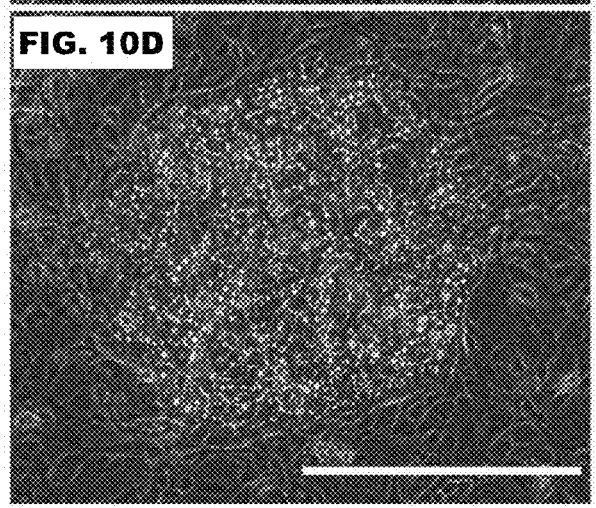
Figure 10E:
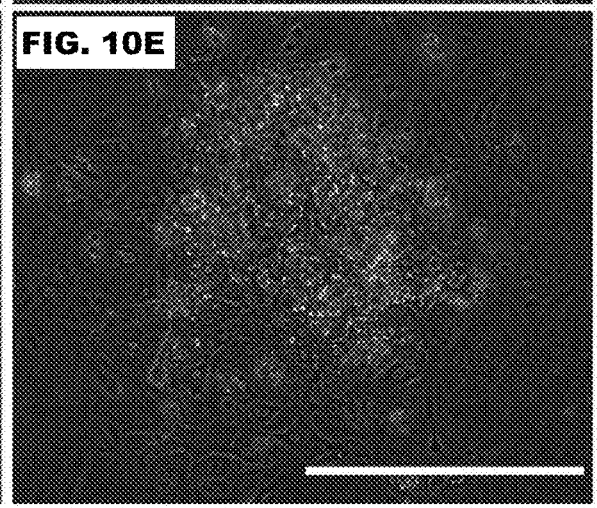
Figure 11A:
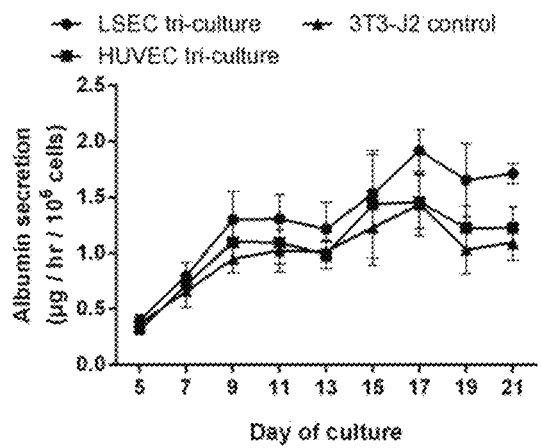
FIG. 11A, FIG. 11B, FIG. 11C and FIG. 11D depict the functionality of hepatocyte/fibroblast/endothelia layered tri-cultures. Tri-cultures of hepatocytes with 3T3-J2 fibroblasts and either liver sinusoidal endothelial cells (LSECs) or human umbilical vein endothelial cells (HUVECs) in the layered configuration were evaluated for (FIG. 11A) albumin secretions, (FIG. 11B) urea secretions, (FIG. 11C) CYP3A4 activity, and (FIG. 11D) CYP2A6 activity. Co-cultures of hepatocytes with 3T3-J2 fibroblasts and pure hepatocytes, both with a Matrigel® overlay, were also included for comparison. Error bars represent standard deviations (n=3).
Figure 11B:
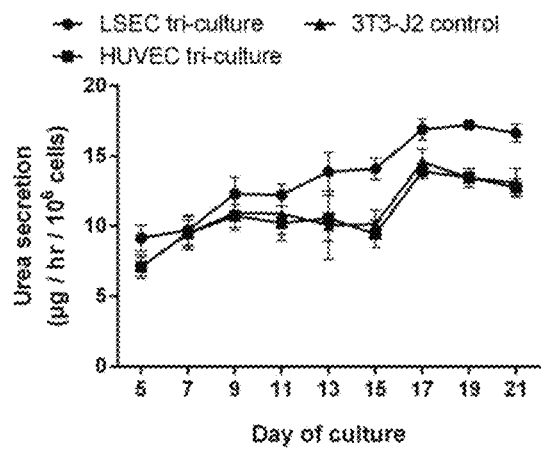
Figure 11C:
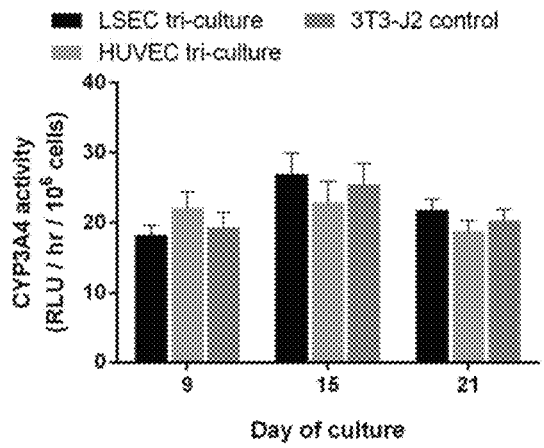
Figure 11D:
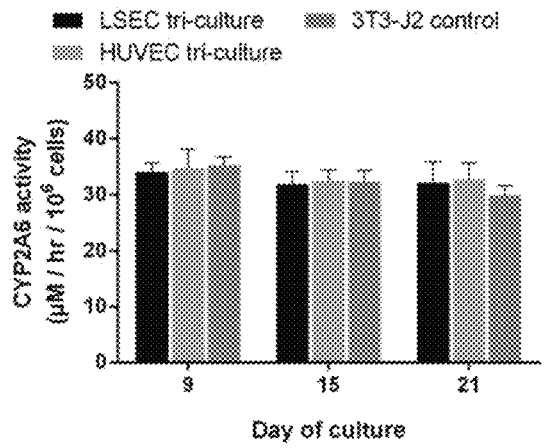

Layered co-cultures of hepatocytes, endothelia, and fibroblasts. Co-culture models were prepared with a layer of Matrigel®. Hepatocytes and fibroblasts were disposed on the substrate which was then layered with Matrigel®. Then, endothelial cells were seeded on top of the Matrigel® (FIG. 10A). After a week of culture, co-cultures of hepatocytes with 3T3-J2 fibroblasts and sinusoidal endothelial cells (LSECs) in the layered configuration (FIG. 10B) and co-cultures of hepatocytes with 3T3-J2 fibroblasts and human umbilical vein endothelial cells (HUVECs) in the layered configuration (FIG. 10C) show a morphology similar to co-cultures of hepatocytes with 3T3-J2 fibroblasts and Matrigel® overlay (FIG. 10D) in terms of polygonal shape and multi-nucleation. In contrast, pure hepatocytes with a Matrigel® overlay are de-differentiated and spread out (FIG. 10E). The function of the layered hepatocyte, endothelia, and fibroblast co-cultures was examined by assaying for albumin secretion, urea secretion and CYP3A4 and CYP2A6 activity. Results demonstrated that the layered co-cultures of hepatocytes, endothelia, and fibroblasts secreted albumin (FIG. 11A) or urea (FIG. 11B) at levels comparable to layered co-cultures of hepatocytes and fibroblasts. Additionally, activity of CYP3A4 (FIG. 11C) and CYP2A6 (FIG. 11D) was comparable in the layered co-cultures with hepatocytes, endothelia, and fibroblasts relative to layered co-cultures with hepatocytes and fibroblasts. Furthermore, in the layered tri-culture model, the endothelial cells had higher acetylated LDL uptake than seen in the non-layered model. This suggests that the composition and/or compliance of the gel overlay plays a role in enhancing endothelial phenotype.

Discussion.

Conventional monolayer cultures of primary human hepatocytes (PHHs), micropatterned co-cultures (MPCCs) of PHHs with 3T3-J2 fibroblasts have been shown to stabilize the hepatic phenotype in vitro. While liver sinusoidal endothelial cells (LSECs) are the major type of non-parenchymal cell found in the liver, it is shown herein that they do not support the hepatocyte phenotype over extended periods. Rather, it is shown that fibroblasts are necessary for supporting normal hepatocyte morphology and function hepatocyte and endothelial cells co-cultures. This is so for HUVECs as well. This suggests that the 3T3-J2 fibroblasts are involved in key processes necessary for stabilizing hepatocyte functionality ex vivo, a requirement for any long-term in vitro study. Without being limited to any one theory, it is speculated that the 3T3-J2 fibroblasts are secreting ECM proteins or soluble factors that have beneficial effects to the hepatic phenotype.

The sourcing of endothelial cells will remain a major consideration for in vitro models of the liver sinusoid. As demonstrated herein, freshly isolated LSECs, HUVECs, or endothelial cell lines can be used. Herein it is shown that freshly isolated LSECs and HUVECs result in normal hepatocyte morphology and function when in co-cultures with hepatocytes and fibroblasts (FIG. 3, FIG. 4), but not in culture with just hepatocytes (FIG. 1, FIG. 2). Additionally, the TMNK cell line has an abnormal morphology in pure hepatocyte cultures (FIG. 8A), but results in increased hepatic functions when co-cultured with hepatocytes and fibroblasts (FIG. 8C, FIG. 8D).

The present disclosure, show that the tri-culture models disclosed herein can be used for discovery and testing of novel therapeutics and for the study of fundamental mechanisms underlying hepatocyte-endothelial interactions. Toxicity studies can also be coupled with efficacy studies to develop both efficacious and safer drugs using the same platform.

What is claimed is:

1. A composition comprising a population of human hepatocytes, a population of murine embryonic fibroblasts, and a population of human endothelial cells selected from human primary liver sinusoidal endothelial cells (LSECs) or human umbilical vein endothelial cells (HUVECs) in co-culture in vitro,
   wherein the hepatocytes are disposed in a micropattern on a culture substrate,
   wherein the micropattern comprises a predetermined two-dimensional pattern of multiple microdots, the micropattern defined by a microdot diameter and an edge-to-edge spacing between each of any two neighboring microdots, and
   wherein the hepatocytes occupy the microdots, the murine embryonic fibroblasts occupy the inter-microdot space, and the population of human endothelial cells is positioned on top of a layer of material comprising at least one extracellular matrix protein that is disposed on the population of human hepatocytes and the population of murine embryonic fibroblasts.

2. The composition of claim 1, further comprising fibronectin.

3. The composition of claim 1, wherein the human hepatocytes are primary human hepatocytes.

4. The composition of claim 1, wherein the human hepatocytes are derived from pluripotent stems cells.

5. The composition of claim 4, wherein the human hepatocytes are derived from induced pluripotent human stem cells.

6. A method of culturing a population of human hepatocytes in vitro, comprising co-culturing the population of human hepatocytes with a population of murine embryonic fibroblasts, and a population of human endothelial cells selected from human primary liver sinusoidal endothelial cells (LSECs) or human umbilical vein endothelial cells (HUVECs),
wherein the hepatocytes are disposed in a micropattern on a culture substrate,
wherein the micropattern comprises a predetermined two-dimensional pattern of multiple microdots, the micropattern defined by a microdot diameter and an edge-to-edge spacing between each of any two neighboring microdots,
wherein the hepatocytes occupy the microdots, the murine embryonic fibroblasts occupy the inter-microdot space, and the population of human endothelial cells is cultured on top of a layer of material comprising at least one extracellular matrix protein that is disposed on the population of human hepatocytes and the population of murine embryonic fibroblasts.

7. The method of claim 6, further comprising co-culturing the population of human hepatocytes with the population of murine embryonic fibroblasts and the population of human endothelial cells with fibronectin.

8. The method according to claim 6, wherein the human hepatocytes are primary human hepatocytes.

9. The method according to claim 6, wherein the human hepatocytes are derived from pluripotent stems cells.

10. The method according to claim 6, wherein the human hepatocytes are derived from induced pluripotent human stem cells.

11. The composition of claim 2, wherein the fibronectin is disposed on the culture substrate.

12. The method of claim 7, wherein the fibronectin is disposed on the culture substrate.

13. The method according to claim 1, wherein the murine embryonic fibroblasts are 3T3-J2 murine embryonic fibroblasts.

* * * * *

SEQUENCE LISTING

```
<160> NUMBER OF SEQ ID NOS: 1

<210> SEQ ID NO 1
<211> LENGTH: 5
<212> TYPE: PRT
<213> ORGANISM: Artificial Sequence
<220> FEATURE:
<223> OTHER INFORMATION: SYNTHESIZED

<400> SEQUENCE: 1

Tyr Ile Gly Ser Arg
1               5
```